(12) United States Patent
Vidal et al.

(10) Patent No.: US 6,379,397 B2
(45) Date of Patent: *Apr. 30, 2002

(54) COMPOSITIONS FOR DYEING KERATINOUS FIBERS COMPRISING PYRAZOLOAZOLES; THEIR USE IN DYEING AS OXIDATION BASE AND DYEING PROCESS; AND NOVEL PYRAZOLOAZOLES

(75) Inventors: Laurent Vidal, Paris; Mireille Maubru, Chatou, both of (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/212,578

(22) Filed: Dec. 16, 1998

(30) Foreign Application Priority Data

Dec. 16, 1997 (FR) ............................. 97 15947

(51) Int. Cl.$^7$ ................................. A61K 7/13

(52) U.S. Cl. ...................... 8/409; 8/406; 8/407; 8/408; 8/423; 8/573

(58) Field of Search ............................. 8/406, 407, 408, 8/409, 423, 573; 548/262.4, 264.2, 264.8, 266.2, 267.2, 267.8, 268.2, 375.1, 376.1, 258

(56) References Cited

U.S. PATENT DOCUMENTS

| | | | |
|---|---|---|---|
| 3,061,432 A | 10/1962 | Menzel et al. | 430/376 |
| 3,227,554 A | 1/1966 | Barr et al. | 430/382 |
| 3,419,391 A | 12/1968 | Young | 430/387 |
| 3,725,067 A | 4/1973 | Bailey et al. | 430/476 |
| 3,926,631 A | 12/1975 | Arai et al. | 430/226 |
| 4,500,632 A | 2/1985 | Ohmura et al. | 430/428 |
| 4,705,863 A | * 11/1987 | Sato et al. | 548/262.4 |
| 4,621,046 A | * 10/1995 | Sato et al. | 548/262.4 |
| 5,457,200 A | * 10/1995 | Zimmermann et al. | 548/262.4 |
| 5,457,210 A | 10/1995 | Kim et al. | 548/262.4 |

FOREIGN PATENT DOCUMENTS

| | | | |
|---|---|---|---|
| DE | 3339201 | * | 5/1984 |
| EP | 0 285 274 | | 10/1988 |
| EP | 0 433 854 | | 6/1991 |
| EP | 0 578 248 | | 1/1994 |
| FR | 2 075 583 | | 10/1971 |
| FR | 2 586 913 | | 3/1987 |
| GB | 1 458 377 | | 12/1976 |
| GB | 2132783 | * | 7/1984 |
| JP | 58-42045 | | 3/1983 |
| JP | 59-99437 | | 6/1984 |
| JP | 59-162548 | | 9/1984 |
| JP | 59-171956 | | 9/1984 |
| JP | 60-33552 | | 2/1985 |
| JP | 60-43659 | | 3/1985 |
| JP | 60-140241 | | 7/1985 |
| JP | 60-172982 | | 9/1985 |
| JP | 60-190779 | | 9/1985 |
| JP | 61-160745 | | 7/1986 |
| JP | 62-129851 | * | 6/1987 |
| JP | 63-74055 | | 4/1988 |
| JP | 2-188748 | | 7/1990 |
| JP | 4-133053 | | 5/1992 |
| WO | WO 93/07849 | | 4/1993 |
| WO | WO 97/35551 | | 10/1997 |

OTHER PUBLICATIONS

CAPLUS Abstract of JP 8–314,055, Konshiroku Photo, Nov. 1996.*
R. Stollé, "Ueber die Ueberführung der secundären Säurehydrazide in Derivate des Furodiazols, Pyrrodiazols und Thiodiazols", Chem. Ber., 32, 797 (1899). No month available.
H. Beyer et al., "Ueber die Pyrazolbildung aus α–Chlor–acetessigester und Thiocarbohydrazid", Chem. Ber., 89, 2550 (1956). No month available.
Joseph Bailey, "Synthesis of 1H–Pyrazolo[3,2–c]–s–Triazoles and Derived Azamethine Dyes", Journal of The Chemical Society, 1977, pp. 2047–2052. No month available.
Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyrimidines", Journal f. prakt. Chemie. Band 320, heft 4,1978, pp. 533–538. No month available.

(List continued on next page.)

*Primary Examiner*—Margaret Einsmann
(74) *Attorney, Agent, or Firm*—Finnegan, Henderson, Farabow, Garrett & Dunner, L.L.P.

(57) ABSTRACT

A composition for dyeing keratinous fibers, in particular human keratinous fibers, such as human hair, containing, in a medium suitable for dyeing:

as oxidation base, at least one compound of formula (I) below:

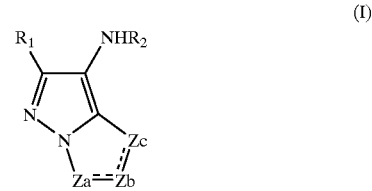

(I)

in which:

$R_1$ is a hydrogen atom, an alkyl radical, an aryl radical, a heterocycle radical, or a halogen atom, $R_2$ is a hydrogen atom, an alkyl radical, a hydroxyalkyl radical, or an aminoalkyl radical, $Z_a$, $Z_b$ and $Z_c$ are independently a nitrogen atom or a carbon carrying an $R_3$ or $R_4$ radical with meanings identical to those of $R_1$; wherein at least one of $Z_a$, $Z_b$ and $Z_c$ is a nitrogen atom; it being possible for $R_3$ and $R_4$ to form between themselves a substituted or unsubstituted aromatic ring.

67 Claims, No Drawings

OTHER PUBLICATIONS

English Language Derwent Abstract of EP 0 433 854, Jun. 1991.

English Language Derwent Abstract of FR 2 075 583, Oct. 1971.

English Language Derwent Abstract of FR 2 586 913, Mar. 1987.

English Language Derwent Abstract of JP 58–42045, Mar. 1983.

English Language Derwent Abstract of JP 59–99437, Jun. 1984.

English Language Derwent Abstract of JP 59–162548, Sep. 1984.

English Language Derwent Abstract of JP–171956, Sep. 1984.

English Language Derwent Abstract of JP 60–43659, Mar. 1985.

English Language Derwent Abstract of JP 60–140241, Jul. 1985.

English Language Derwent Abstract of JP 60–172982, Sep. 1985.

English Language Derwent Abstract of JP 60–190779, Sep. 1985.

English Language Derwent Abstract of JP 61–160745, Jul. 1986.

English Language Derwent Abstract of JP 62–129851, Jun. 1987.

English Language Derwent Abstract of JP 63–74055, Apr. 1988.

English Language Derwent Abstract of JP 2–188748, Jul. 1990.

English Language Derwent Abstract of JP 4–133053, May 1992.

* cited by examiner

COMPOSITIONS FOR DYEING KERATINOUS FIBERS COMPRISING PYRAZOLOAZOLES; THEIR USE IN DYEING AS OXIDATION BASE AND DYEING PROCESS; AND NOVEL PYRAZOLOAZOLES

The invention relates to a composition for the oxidation dyeing of keratinous fibers, and in particular of human keratinous fibers such as human hair, comprising at least one pyrazoloazole compound as an oxidation base, the method of dyeing which employs this composition, and novel pyrazoloazoles.

It is well known to dye keratinous fibers, and in particular human hair, using dyeing compositions comprising oxidation dye precursors, such as ortho- or para-phenylenediamines, ortho- or para-aminophenols, and heterocyclic compounds, which are generally referred to as oxidation bases. The oxidation dye precursors, or oxidation bases, are colorless or lightly colored compounds which, when combined with oxidizing products, can give rise, by an oxidative coupling process, to colored and coloring compounds.

It is also known that the shades obtained with these oxidation bases can be varied by combining them with couplers or coloring modifiers, the latter being chosen in particular from aromatic meta-diamines, meta-aminophenols, meta-diphenols and certain heterocyclic compounds, such as indole compounds.

The diversity of the molecules employed as oxidation bases and couplers makes it possible to obtain a wide range of colors.

The "permanent" coloration obtained by these oxidation dyes should optimally meet certain conditions. Thus, it should have no toxicological effects, should allow shades of the desired intensity to be obtained, and should have good resistance to external agents (light, bad weather, washing, permanent waving, perspiration or rubbing).

The dyes should also allow white hairs to be covered and, finally, they should be as unselective as possible, that is to say, they should allow the smallest possible differences in coloration to be produced over the entire length of a single keratinous fibre, which may vary in condition of sensitization or damage from its tip to its root. They should also exhibit good chemical stability in the formulations and a good toxicological profile.

The inventors have discovered that it is possible to obtain powerful novel dyes which are not very selective, are particularly resistant to various external agents which keratinous fibers can be subjected to, and which are capable of generating intense colorings in varied shades by using, as oxidation base, pyrazoloazole compounds of formula (I) defined below.

This discovery is the basis of the present invention.

The first aspect of the invention is thus a composition for the oxidation dyeing of keratinous fibers, and in particular human keratinous fibers such as hair, comprising, in a medium suitable for dyeing:

as oxidation base, at least one pyrazoloazole compound of formula (I) or at least one acid addition salt thereof:

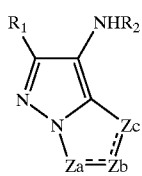

(I)

in which:

$R_1$ represents: a hydrogen atom; a linear or branched $C_1$–$C_{20}$ alkyl radical, optionally substituted by 1 or 2 radicals R chosen from a halogen atom, a nitro radical, a cyano radical, a hydroxyl radical, an alkoxy radical, an aryloxy radical, an amino radical, an alkylamino radical, an acylamino radical, a carbamoyl radical, a sulphonamido radical, a sulphamoyl radical, an imido radical, an alkylthio radical, an arylthio radical, an aryl radical, such as phenyl or naphthyl, a ($C_1$–$C_4$)alkoxy-carbonyl radical and an acyl radical; an aryl radical (such as phenyl or naphthyl), optionally substituted by 1 or 2 radicals R as defined above; a 5- or 6-membered heterocycle containing at least one nitrogen, oxygen or sulphur atom (such as pyridyl, quinolyl, pyrrolyl, morpholyl, furanyl, tetrahydrofuranyl, pyrazolyl, triazolyl, tetrazolyl, thiazolyl, oxazolyl, imidazolyl or thiadiazolyl), wherein said heterocycle is optionally substituted by 1 or 2 radicals R as defined above;

when $R_1$ denotes a $C_1$–$C_4$ alkyl radical, an aryl radical or a 5- or 6-membered heterocycle (as defined above), it can be connected to the carbon atom of the pyrazole via an oxygen, nitrogen or sulphur atom (in this case, $R_1$ becomes $XR_1$ with X=O, NH or S);

$R_1$ can, additionally, denote a halogen atom (such as bromine, chlorine or fluorine); an acyl radical; a sulphonyl radical; a sulphinyl radical; a phosphonyl radical; a carbamoyl radical; a sulphamoyl radical; a cyano radical; a siloxy radical; an amino radical; an acylamino radical; an acyloxy radical; a carbamoyloxy radical; a sulphonamide radical; an imide radical; a ureido radical; a sulphamoylamino radical; a ($C_1$–$C_4$) alkoxy-carbonylamino radical; an aryloxycarbonylamino radical; a ($C_1$–$C_4$)alkoxy-carbonyl radical; an aryloxycarbonyl radical; a carboxyl radical; or a hydroxyl radical; $R_2$ denotes a hydrogen atom; a $C_1$–$C_4$ alkyl radical; a $C_1$–$C_4$ monohydroxyalkyl radical; a $C_2$–$C_4$ polyhydroxyalkyl radical; a $C_1$–$C_4$ aminoalkyl radical; a $(CH_2)_p$—X—$(CH_2)_q$OR' radical in which p and q are identical or different integers ranging from 1 to 3, R' represents a hydrogen atom or a methyl radical, and X denotes an oxygen atom or an NR" group in which R" represents a hydrogen atom or a methyl radical; a ($C_1$–$C_4$)alkoxy($C_2$–$C_4$)alkyl radical; or a di($C_1$–$C_4$)alkylamino($C_1$–$C_4$)alkyl radical; and $Z_a$, $Z_b$, and $Z_c$ represent, independently of one another, a nitrogen atom or a carbon atom carrying an $R_3$ or $R_4$ radical, where $R_3$ and $R_4$ have the same meanings as those indicated above for the $R_1$ radical, with the proviso that at least one of the $Z_a$, $Z_b$, and $Z_c$ radicals is other than a carbon atom; $R_3$ and $R_4$ can also together form a substituted or unsubstituted aromatic ring, such as a phenyl ring.

Preferred $R_1$ radicals of the compounds of formula (I) defined above are chosen from a hydrogen atom; a linear or branched $C_1$–$C_4$ alkyl radical; a phenyl ring; a phenyl ring substituted by a halogen atom, a $C_1$–$C_4$ alkyl radical, a $C_1$–$C_4$ alkoxy radical, a nitro radical, an amino radical, a trifluoromethyl radical or a $C_1$–$C_4$ alkylamino radical; a benzyl radical; a benzyl radical substituted by a halogen atom, a $C_1$–$C_4$ alkyl radical, a $C_1$–$C_4$ alkoxy radical, a nitro radical, an amino radical, a trifluoromethyl radical or a $C_1$–$C_4$ alkylamino radical; a heterocycle chosen from the thiophene, furan or pyridine rings; a trifluoromethyl radical; a $(CH_2)_p$—X—$(CH_2)_q$—OR' radical in which p and q are identical or different integers ranging from 1 to 3, where R' represents a hydrogen atom or a methyl radical and X denotes an oxygen atom or an NR" radical in which R" denotes a hydrogen atom or a methyl radical; a $C_1$–$C_4$ hydroxyalkyl radical; a $C_1-C_4$ aminoalkyl radical; a $C_1-C_4$ alkylamino radical; a di($C_1-C_4$)alkylamino radical; an arylamino radical; an alkoxy radical chosen from methoxy, ethoxy and phenoxy; a halogen atom chosen from bromine, chlorine and fluorine; a carboxyl group; a $C_1-C_4$ alkoxycarbonyl radical; a phenyloxycarbonyl radical; a methylthio radical; an ethylthio radical; a phenylthio radical; a methanesulphonyl radical; a cyano radical; an amino radical; or a hydroxyl radical.

More preferred $R_1$ radicals of the compounds of formula (I) defined above are chosen from a hydrogen atom; an alkyl radical chosen from the methyl, ethyl, isopropyl and tert-butyl radicals; a halogen atom chosen from chlorine and fluorine; a phenyl radical; a toluyl radical; a 4-chlorophenyl radical; a 4-methoxyphenyl radical; a 3-methoxyphenyl radical; a 2-methoxyphenyl radical; a benzyl radical; a heterocycle chosen from the pyridyl, furyl and thienyl rings; a trifluoromethyl radical, a hydroxymethyl radical; an aminomethyl radical; a methoxy radical; an ethoxy radical; a methylamino radical; an ethylamino radical; a dimethylamino radical; a carboxyl radical; a methoxycarbonyl radical; an ethoxycarbonyl radical and a cyano radical.

More particularly preferred $R_1$ radicals are chosen from: a hydrogen atom; a chlorine atom; a methyl radical; an ethyl radical; a phenyl radical; a toluyl radical; a 4-chlorophenyl radical; a 4-methoxyphenyl radical; a benzyl radical; a trifluoromethyl radical; a methoxy radical; an ethoxy radical; a carboxyl radical; a methylamino radical; a dimethylamino radical and a cyano radical. Preferred $R_2$ radicals of the compounds of formula (I) defined above are chosen from a hydrogen atom; a methyl radical and a β-hydroxyethyl radical.

More preferably, the $R_2$ radical represents a hydrogen atom.

Preferred $R_3$ and $R_4$ radicals of the compounds of formula (I) defined above are chosen from a hydrogen atom; a hydroxyl radical; an amino radical; a linear or branched $C_1-C_4$ alkyl radical; a trifluoromethyl radical; a phenyl ring; a phenyl ring substituted by one or two radicals R chosen from a halogen atom, a $C_1-C_4$ alkyl radical, a $C_1-C_4$ alkoxy radical, a hydroxyl radical, a carboxyl radical, a nitro radical, a $C_1-C_4$ alkylthio radical, a methylenedioxy radical, an amino radical, a trifluoromethyl radical and a $C_1-C_4$ alkylamino radical; a benzyl radical; a benzyl radical substituted by a halogen atom, a methyl or isopropyl radical or a methoxy radical; a $C_1-C_4$ monohydroxyalkyl radical; a $C_1-C_4$ aminoalkyl radical; a ($C_1-C_4$)alkylamino($C_1-C_4$) alkyl radical; an alkoxy radical chosen from the methoxy, ethoxy and phenoxy radicals; a methylthio radical; an ethylthio radical; a phenylthio radical; a methanesulphonyl radical; or a substituted or unsubstituted aromatic ring formed jointly by $R_3$ and $R_4$, such as a phenyl ring, pyridyl ring or phenyl ring substituted by a sulphonyl radical, a halogen atom, a $C_1-C_4$ alkoxy radical, a $C_1-C_4$ alkyl radical, a nitro radical, a cyano radical, an amino radical, a $C_1-C_4$ alkylamino radical or a trifluoromethyl radical.

More preferred $R_3$ and $R_4$ radicals of the compounds of formula (I) defined above are chosen from a hydrogen atom; an alkyl radical chosen from the methyl, ethyl, isopropyl, n-propyl and tert-butyl radicals; a phenyl ring; a toluyl ring; a 2-, 3- or 4-chlorophenyl ring; a 3- or 4-hydroxyphenyl ring; a 3- or 4-aminophenyl ring; a 3- or 4-methoxyphenyl ring; a 4-trifluoromethylphenyl ring; a benzyl ring; a trifluoromethyl radical; a hydroxymethyl radical; a hydroxyethyl radical; a hydroxyisopropyl radical; an aminomethyl or aminoethyl radical; a methoxy or ethoxy radical; a methylthio or ethylthio radical; or a substituted or unsubstituted aromatic ring formed jointly by $R_3$ and $R_4$, such as a phenyl, toluyl, sulphonylphenyl and chlorophenyl ring.

More particularly preferred $R_3$ and $R_4$ radicals are chosen from a hydrogen atom; a methyl radical; an ethyl radical; an isopropyl radical; a phenyl ring; a 4-chlorophenyl ring; a 4-methoxyphenyl ring; a 4-aminophenyl ring; a methoxy or ethoxy radical; a methylthio or ethylthio radical and a phenyl ring formed jointly by $R_3$ and $R_4$.

Preferred compounds of formula (I) in accordance with the invention, are:

i) the pyrazolo[1,5-b]-1,2,4-triazoles of formula (Ia) and the acid addition salts thereof:

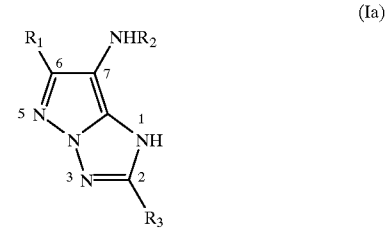

(Ia)

ii) the pyrazolo[3,2-c]-1,2,4-triazoles of formula (Ib) and the acid addition salts thereof:

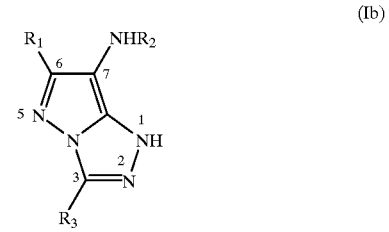

(Ib)

iii) the pyrazolotetrazoles of formula (Ic) the acid addition salts thereof:

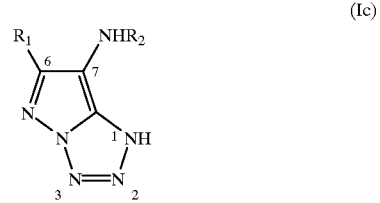

(Ic)

iv) the pyrazolo[1,5-a]imidazoles of formula (Id) and the acid addition salts:

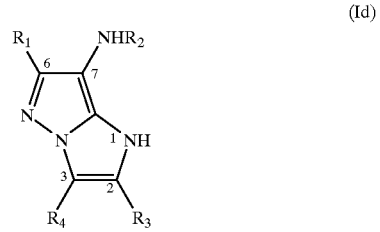

(Id)

(v) the pyrzolo[5,1-e]pyrazoles of formula (Ie) and the acid addition salts:

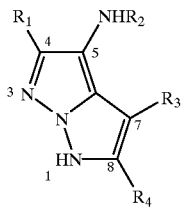

(Ie)

vi) the pyrazolo[5,1-e]-1,2,3-triazoles of formula (If) and the acid addition salts thereof:

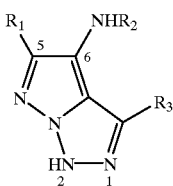

(If)

in which $R_1$, $R_2$, $R_3$ and $R_4$ have the same meanings as those indicated above for formula (I).

Preferred compounds of formulae (Ia) and (Ib), are those in which:
- $R_1$ denotes a hydrogen atom or a methyl, trifluoromethyl, carboxyl, phenyl, ethoxy, cyano, ethylthio, amino or hydroxyl radical;
- $R_2$ denotes a hydrogen atom;
- $R_3$ denotes a hydrogen atom or a methyl, β-aminoethyl, ethyl, isopropyl, phenyl, β-hydroxyethyl, methylthio or ethoxy radical.

Preferred compounds of formula (Ic), are those in which:
- $R_1$ denotes a hydrogen atom or a methyl, trifluoromethyl, carboxyl, phenyl, ethoxy or cyano radical;
- $R_2$ denotes a hydrogen atom.

Preferred compounds of formula (Id), are those in which:
- $R_1$ denotes a hydrogen atom or a methyl, trifluoromethyl, carboxyl, phenyl, ethoxy, cyano, amino, ethylthio or hydroxyl radical;
- $R_2$ denotes a hydrogen atom;
- $R_3$ and $R_4$ respectively denote a hydrogen atom and a hydrogen atom, a hydrogen atom and a methyl radical, a methyl radical and a hydrogen atom, a hydrogen atom and a phenyl radical, or a hydroxyl radical and a hydrogen atom; or $R_3$ and $R_4$ jointly form a phenyl ring.

Preferred compounds of formula (Ie), are those in which:
- $R_1$ denotes a hydrogen atom or a methyl, trifluoromethyl, carboxyl, phenyl, ethoxy or cyano radical;
- $R_2$ denotes a hydrogen atom;
- $R_3$ and $R_4$ respectively denote a hydrogen atom and a methyl radical, a methyl radical and a hydrogen atom, a methyl radical and a methyl radical, a hydrogen atom and a phenyl radical, or a hydrogen atom and an amino radical. Preferred compounds of formula (If), are those in which:
- $R_1$ denotes a hydrogen atom or a methyl, trifluoromethyl, carboxyl, phenyl, ethoxy or cyano radical;
- $R_2$ denotes a hydrogen atom;
- $R_3$ denotes a hydrogen atom or a methyl radical.

Preferred compounds of formulae (Ia) which can be used in the dyeing compositions, in accordance with the invention, are:
7-amino-2-methylpyrazolo[1,5-b]-1,2,4-triazole;
7-amino-2-ethylpyrazolo[1,5-b]-1,2,4-triazole;
7-amino-2-isopropylpyrazolo[1,5-b]-1,2,4-triazole;
7-amino-2-phenylpyrazolo[1,5-b]-1,2,4-triazole;
7-amino-2,6-dimethylpyrazolo[1,5-b]-1,2,4-triazole;
7-amino-6-methyl-2-ethylpyrazolo[1,5-b]-1,2,4-triazole;
7-amino-6-methyl-2-isopropylpyrazolo[1,5-b]-1,2,4-triazole;
7-amino-6-methyl-2-phenylpyrazolo[1,5-b]-1,2,4-triazole;
7-amino-6-carboxy-2-methylpyrazolo[1,5-b]-1,2,4-triazole;
7-amino-6-carboxy-2-ethylpyrazolo[1,5-b]-1,2,4-triazole;
7-amino-6-carboxy-2-isopropylpyrazolo[1,5-b ]-1,2,4-triazole;
7-amino-6-carboxy-2-phenylpyrazolo[1,5-b]-1,2,4-triazole;
7-amino-6-phenyl-2-methylpyrazolo[1,5-b]-1,2,4-triazole;
7-amino-6-phenyl-2-ethylpyrazolo[1,5-b]-1,2,4-triazole;
7-amino-6-phenyl-2-isopropylpyrazolo[1,5-b]-1,2,4-triazole;
6,7-diamino-2-methylpyrazolo[1,5-b]-1,2,4-triazole;
6,7-diamino-2-ethylpyrazolo[1,5-b]-1,2,4-triazole;
6,7-diamino-2-isopropylpyrazolo[1,5-b]-1,2,4-triazole;
6,7-diamino-2-phenylpyrazolo[1,5-b]-1,2,4-triazole;
7-amino-6-ethylthio-2-methylpyrazolo[1,5-b]-1,2,4-triazole;
7-amino-6-ethylthio-2-ethylpyrazolo[1,5-b]-1,2,4-triazole;
7-amino-6-ethylthio-2-isopropylpyrazolo[1,5-b]-1,2,4-triazole;
7-amino-6-ethylthio-2-phenylpyrazolo[1,5-b]-1,2,4-triazole;
7-amino-6-ethoxy-2-methylpyrazolo[1,5-b]-1,2,4-triazole;
7-amino-6-ethoxy-2-ethylpyrazolo[1,5-b]-1,2,4-triazole;
7-amino-6-ethoxy-2-isopropylpyrazolo[1,5-b]-1,2,4-triazole;
7-amino-6-ethoxy-2-phenylpyrazolo[1,5-b]-1,2,4-triazole;
7-amino-6-methyl-2-(2'-aminoethyl)pyrazolo[1,5-b]-1,2,4-triazole;
7-amino-6-carboxy-2-(2'-aminoethyl)pyrazolo[1,5-b]-1,2,4-triazole;
7-amino-6-phenyl-2-(2'-aminoethyl)pyrazolo[1,5-b]-1,2,4-triazole;
7-amino-6-ethylthio-2-(2'-aminoethyl)pyrazolo[1,5-b]-1,2,4-triazole;
7-amino-2-(2'-aminoethyl)pyrazolo[1,5-b]-1,2,4-triazole;
7-amino-2-(2'-hydroxyethyl)pyrazolo[1,5-b]-1,2,4-triazole;
7-amino-6-methyl-2-(2'-hydroxyethyl)pyrazolo[1,5-b]-1,2,4-triazole;
7-amino-6-ethylthio-2-(2'-hydroxyethyl)pyrazolo[1,5-b]-1,2,4-triazole;
7-amino-6-carboxy-2-(2'-hydroxyethyl)pyrazolo[1,5-b]-1,2,4-triazole;
7-amino-6-phenyl-2-(2'-hydroxyethyl)pyrazolo[1,5-b]-1,2,4-triazole;
6,7-diamino-2-(2'-aminoethyl)pyrazolo[1,5-b]-1,2,4-triazole;
6,7-diamino-2-(2'-hydroxyethyl)pyrazolo[1,5-b]-1,2,4-triazole;
7-amino-6-ethoxy-2-(2'-aminoethyl)pyrazolo[1,5-b]-1,2,4-triazole;
7-amino-6-ethoxy-2-(2'-hydroxyethyl)pyrazolo[1,5-b]-1,2,4-triazole;
and the acid addition salts thereof.

Preferred compounds of formulae (Ib) which can be used in the dyeing compositions, in accordance with the invention, are:

7-amino-3-methylpyrazolo[3,2-c]-1,2,4-triazole;
7-amino-3-ethylpyrazolo[3,2-c]-1,2,4triazole;
7-amino-3-isopropylpyrazolo[3,2-c]-1,2,4-triazole;
7-amino-3-phenylpyrazolo[3,2-c]-1,2,4-triazole;
7-amino-3-(2'-aminoethyl)pyrazolo[3,2-c]-1,2,4-triazole;
7-amino-3-(2'-hydroxyethyl)pyrazolo[3,2-c]-1,2,4-triazole;
7-amino-6-methyl-3-ethylpyrazolo[3,2-c]-1,2,4-triazole;
7-amino-3,6-dimethylpyrazolo[3,2-c]-1,2,4-triazole;
7-amino-6-methyl-3-isopropylpyrazolo[3,2-c]-1,2,4-triazole;
7-amino-6-methyl-3-phenylpyrazolo[3,2-c]-1,2,4-triazole;
7-amino-6-methyl-3-(2'-aminoethyl)pyrazolo[3,2-c]-1,2,4triazole;
7-amino-6-methyl-3-(2'-hydroxyethyl)pyrazolo[3,2-c]-1,2,4-triazole;
7-amino-6-methyl-3-(methylthio)pyrazolo[3,2-c]-1,2,4-triazole;
7-amino-6-phenyl-3-methylpyrazolo[3,2-c]-1,2,4-triazole;
7-amino-6-phenyl-3-ethylpyrazolo[3,2-c]-1,2,4-triazole;
7-amino-6-phenyl-3-isopropylpyrazolo[3,2-c]-1,2,4-triazole;
7-amino-6-phenyl-3-phenylpyrazolo[3,2-c]-1,2,4-triazole;
7-amino-6-phenyl-3-(2'-aminoethyl)pyrazolo[3,2-c]-1,2,4-triazole;
7-amino-6-phenyl-3-(2'-hydroxyethyl)pyrazolo[3,2-c]-1,2,4-triazole;
7-amino-6-phenyl-3-(methylthio)pyrazolo[3,2-c]-1,2,4-triazole;
7-amino-6-ethylthio-3-methylpyrazolo[3,2-c]-1,2,4-triazole;
7-amino-6-ethylthio-3-ethylpyrazolo[3,2-c]-1,2,4-triazole;
7-amino-6-ethylthio-3-isopropylpyrazolo[3,2-c]-1,2,4-triazole;
7-amino-6-ethylthio-3-phenylpyrazolo[3,2-c]-1,2,4-triazole;
7-amino-6-ethylthio-3-(2'-aminoethyl)pyrazolo[3,2-c]-1,2,4-triazole;
7-amino-6-ethylthio-3-(2'-hydroxyethyl)pyrazolo[3,2-c]-1,2,4-triazole;
7-amino-6-trifluoromethyl-3-(methylthio)pyrazolo[3,2-c]-1,2,4-triazole;
7-amino-6-(trifluoromethyl)pyrazolo[3,2-c]-1,2,4-triazole;
7-amino-6-carboxy-3-methylpyrazolo[3,2-c]-1,2,4-triazole;
7-amino-6-carboxy-3-ethylpyrazolo[3,2-c]-1,2,4-triazole;
7-amino-6-carboxy-3-isopropylpyrazolo[3,2-c]-1,2,4-triazole;
7-amino-6-carboxy-3-phenylpyrazolo[3,2-c]-1,2,4-triazole;
7-amino-6-carboxy-3-(2'-aminoethyl)pyrazolo[3,2-c]-1,2,4-triazole;
7-amino-6-carboxy-3-(2'-hydroxyethyl)pyrazolo[3,2-c]-1,2,4-triazole;
6,7-diamino-3-methylpyrazolo[3,2-c]-1,2,4-triazole;
6,7-diamino-3-ethylpyrazolo[3,2-c]-1,2,4-triazole;
6,7-diamino-3-phenylpyrazolo[3,2-c]-1,2,4-triazole;
6,7-diamino-3-isopropylpyrazolo[3,2-c]-1,2,4-triazole;
7-amino-6-ethoxy-3-methylpyrazolo[3,2-c]-1,2,4-triazole;
7-amino-6-ethoxy-3-ethylpyrazolo[3,2-c]-1,2,4-triazole;
7-amino-6-ethoxy-3-isopropylpyrazolo[3,2-c]-1,2,4-triazole;
7-amino-6-ethoxy-3-phenylpyrazolo[3,2-c]-1,2,4-triazole;
7-amino-6-ethoxy-3-(2'-aminoethyl)pyrazolo[3,2-c]-1,2,4-triazole;
7-amino-6-ethoxy-3-(2'-hydroxyethyl)pyrazolo[3,2-c]-1,2,4-triazole;
6,7-diamino-3-(2'-aminoethyl)pyrazolo[3,2-c]-1,2,4-triazole;
6,7-diamino-3-(2'-hydroxyethyl)pyrazolo[3,2-c]-1,2,4-triazole;
and the acid addition salts thereof.

Preferred compounds of formulae (Ic) which can be used in the dyeing compositions, in accordance with the invention, are:
7-amino-6-methylpyrazolo[5,1-e]tetrazole;
7-amino-6-phenylpyrazolo[5,1-e]tetrazole;
7-amino-6-carboxypyrazolo[5,1-e]tetrazole;
and the acid addition salts thereof.

Preferred compounds of formulae (Id) which can be used in the dyeing compositions in accordance with the invention, are:
7-amino-2-methylpyrazolo[1,5-a]imidazole;
7-amino-2-phenylpyrazolo[1,5-a]imidazole;
7-aminopyrazolo[1,5-a]benzimidazole;
7-amino-6-methylpyrazolo[1,5-a]imidazole;
7-amino-2,6-dimethylpyrazolo[1,5-a]imidazole;
7-amino-6-methyl-2-phenylpyrazolo[1,5-a]imidazole;
7-amino-6-methylpyrazolo[1,5-a]benzimidazole;
7-amino-6-phenylpyrazolo[1,5-a]imidazole;
7-amino-6-phenyl-2-methylpyrazolo[1,5-a]imidazole;
7-amino-2,6-diphenylpyrazolo[1,5-a]imidazole;
7-amino-6-phenylpyrazolo[1,5-a]benzimidazole;
7-amino-6-carboxypyrazolo[1,5-a]imidazole;
7-amino-6-carboxy-2-methylpyrazolo[1,5-a]imidazole;
7-amino-6-carboxy-2-phenylpyrazolo[1,5-a]imidazole;
7-amino-6-carboxypyrazolo[1,5-a]benzimidazole;
7-amino-6-ethoxypyrazolo[1,5-a]imidazole;
7-amino-6-ethoxy-2-methylpyrazolo[1,5-a]imidazole;
7-amino-6-ethoxy-2-phenylpyrazolo[1,5-a]imidazole;
7-amino-6-ethoxypyrazolo[1,5-a]benzimidazole;
7-amino-6-(trifluoromethyl)pyrazolo[1,5-a]benzimidazole;
7-amino-6-aminopyrazolo[1,5-a]imidazole;
7-amino-6-amino-2-methylpyrazolo[1,5-a]imidazole;
7-amino-6-amino-2-phenylpyrazolo[1,5-a]imidazole;
7-amino-6-aminopyrazolo[1,5-a]benzimidazole;
7-amino-6-(ethylthio)pyrazolo[1,5-a]imidazole;
7-amino-6-ethylthio-2-methylpyrazolo[1,5-a]imidazole;
7-amino-6-ethylthio-2-phenylpyrazolo[1,5-a]imidazole;
7-amino-6-methyl-2-hydroxypyrazolo[1,5-a]imidazole;
7-amino-6-phenyl-2-hydroxypyrazolo[1,5-a]imidazole;
7-amino-6-ethoxy-2-hydroxypyrazolo[1,5-a]imidazole;
7-amino-6-ethylthio-2-hydroxypyrazolo[1,5-a]imidazole;
6,7-diamino-2-hydroxypyrazolo[1,5-a]imidazole;
and the acid addition salts thereof.

Preferred compounds of formulae (Ie) which can be used in the dyeing compositions in accordance with the invention, are:
5,8-diamino-4-methylpyrazolo[5,1-e]pyrazole;
5,7,8-triamino-4-methylpyrazolo[5,1-e]pyrazole;
and the acid addition salts thereof.

Preferred compounds of formulae (If) which can be used in the dyeing compositions in accordance with the invention, are:
6-amino-5-methylpyrazolo[5,1-e]-1,2,3-triazole;
6-amino-5-phenylpyrazolo[5,1-e]-1,2,3-triazole;
and the acid addition salts thereof.

The pyrazoloazole compound(s) formula (I) preferably represent(s) from 0.0005 to 12% by weight approximately relative to the total weight of the dyeing composition, and more preferably, from 0.005 to 6% by weight, approximately, of the total weight.

The medium (or vehicle) suitable for dyeing is, for example, water, a water/alcohol mixture, or a mixture of water and of at least one organic solvent to dissolve any compounds which are not be sufficiently water soluble. Preferred organic solvents are, for example, $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether, diethylene glycol monomethyl ether, and aromatic alcohols, such as benzyl alcohol or phenoxyethanol, and mixtures thereof.

The solvents can be present in proportions ranging from 1 to 40% by weight approximately relative to the total weight of the dyeing composition, and even more preferably from 5 to 30% by weight approximately.

The pH of the dyeing composition in accordance with the invention generally ranges from 3 to 12, approximately, and preferably approximately from 5 to 11. It can be adjusted to the desired value by means of acidifying or basifying agents commonly used in dyeing keratinous fibers, or alternatively using conventional buffer systems.

Preferred acidifying agents include, for example, inorganic and organic acids, such as hydrochloric acid, orthophosphoric acid, sulphuric acid, carboxylic acids, such as acetic acid, tartaric acid, citric acid or lactic acid, and sulphonic acids.

Preferred basifying agents include, for example, aqueous ammonia, alkaline carbonates, alkanolamines, such as mono-, di- and triethanolamines and derivatives thereof, sodium hydroxide, potassium hydroxide, and the compounds of following formula (II):

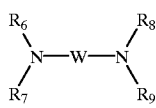

(II)

in which W is a propylene residue optionally substituted by a hydroxyl radical or a $C_1$–$C_4$ alkyl radical; and $R_6$, $R_7$, $R_8$ and $R_9$, which are identical or different, represent a hydrogen atom, a $C_1$–$C_4$ alkyl radical or $C_1$–$C_4$ hydroxyalkyl radical.

In a preferred embodiment, the dyeing composition in accordance with the invention additionally includes at least one coupler in order to modify or enrich with highlights the shades obtained by employing the compounds of formula (I).

The couplers which can be used in the dyeing composition in accordance with the invention may be chosen from the couplers used conventionally in oxidation dyeing, among which generally preferred couplers are: meta-phenylenediamines, meta-aminophenols, meta-diphenols and heterocyclic couplers.

More particularly preferred couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl)amino-1-methoxybenzene, 1,3-diaminobenzene, 1,3-bis(2,4-diaminophenoxy)-propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, and the acid addition salts thereof.

When present, the coupler(s) preferably represent(s) from 0.0001 to 10% by weight approximately relative to the total weight of the dyeing composition, and even more preferably from 0.005 to 5% by weight approximately relative to this weight.

The dyeing composition in accordance with the invention may additionally comprise, as well as the above-defined dyes, at least one additional oxidation base chosen from the oxidation bases which are conventionally employed in oxidation dyeing, among which preferred oxidation bases are: para-phenylenediamines, bisphenylalkylenediamines, para-aminophenols, ortho-aminophenols and heterocyclic bases which are different from the pyrazoloazole compounds of formula (I) used in accordance with the invention.

Among the para-phenylenediamines, preferred para-phenylenediamine are: para-phenylenediamines, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediameine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, and the acid addition salts thereof.

Among the abovementioned para-phenylenediamines, more preferred para-phenylenediamines are: para-phenylenediamine, para-toluylenediamine, 2-isopropyl-para-phenylenediamine, para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and the acid addition salts thereof.

Among the bisphenylalkylenediamines, preferred bisphenylalkylenediamines are: N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid addition salts thereof.

Among the para-aminophenols, preferred para-aminophenols are: para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)-aminomethyl]phenol, 4-amino-2-fluorophenol, and the acid addition salts thereof.

Among the ortho-aminophenols, preferred ortho-aminophenols are: 2-aminophenol, 2-amino-5-methylphenol, 2-amino-6-methylphenol, 5-acetamido-2-aminophenol, and the acid addition salts thereof.

Among the heterocyclic bases, preferred heterocyclic bases are: pyridine derivatives, pyrimidine derivatives and pyrazole derivatives.

When used, the additional oxidation base(s) preferably represent(s) from 0.0005 to 12% by weight approximately relative to the total weight of the dyeing composition and, more preferably from 0.005 to 6% by weight approximately relative to this weight.

The acid addition salts used within the scope of the dyeing compositions of the invention (compounds of formula (I), additional oxidation bases and couplers) are chosen in particular from hydrochlorides, hydrobromides, sulphates, citrates, succinates, tartrates, tosylates, benzenesulphonates, lactates and acetates.

The dyeing composition in accordance with the invention can additionally contain one or more direct dyes which can be chosen from nitrated dyes of the benzene series.

The dyeing composition in accordance with the invention can also contain various adjuvants used conventionally used in hair dyeing compositions, such as anionic, cationic, non-ionic, amphoteric or zwitterionic surfactants or mixtures thereof, anionic, cationic, non-ionic, amphoteric or zwitterionic polymers or mixtures thereof, inorganic or organic thickeners, antioxidants, penetration agents, sequesterants, fragrances, buffers, dispersants, conditioners such as, for example, modified or non-modified, volatile or non-volatile silicones, film formers, ceramides, preservatives or opacifiers.

Of course, a person skilled in the art will take care to choose the optional additional compound(s) such that the advantageous properties intrinsically associated with the dyeing composition in accordance with the invention are not, or not substantially, adversely affected by the additions envisaged.

The dyeing composition according to the invention may be in various forms, such as in the form of liquids, creams or gels, or any other form which is suitable for dyeing keratinous fibers, and in particular human hair.

Another aspect of the invention is the use of the compounds of formula (I) as defined above as oxidation base in compositions for the oxidation dyeing of keratinous fibers, and in particular human keratinous fibers, such as hair.

The invention also provides a process for dyeing keratinous fibers, and in particular of human keratinous fibers such as hair using the dyeing composition as defined above.

According to this process, at least one dyeing composition as defined above is applied to the fibers for a period which is sufficient to develop the desired coloration, either in air or with the aid of an oxidizing agent.

According to one embodiment of the process of the invention, the dyeing of the fibers can be carried out without the addition of an oxidizing agent, solely by contact with the oxygen in the air. In this case, the dyeing composition can optionally include oxidation catalysts in order to accelerate the oxidation process.

A preferred oxidation catalyst is, for example, a metal salt, such as manganese, cobalt, copper, iron, silver and zinc. A more preferred oxidation catalyst is, for example, manganese diacetate tetrahydrate, manganese dichloride, manganese triacetate and its hydrates, manganese trichloride, zinc dichloride, zinc diacetate dihydrate, zinc carbonate, zinc dinitrate, zinc sulphate, iron dichloride, iron sulphate, iron diacetate, cobalt diacetate tetrahydrate, cobalt carbonate, cobalt dichloride, cobalt sulphate heptahydrate, cupric chloride or ammoniacal silver nitrate.

When used, the metal salt generally represent from 0.001 to 4% by weight of relative to the total weight of the dyeing composition, and more preferably from 0.005 to 2% by weight relative to the total weight of the dyeing composition.

According to another embodiment of the process of the invention, at least one dyeing composition as defined above is applied to the fibers, the color being developed at an acidic, neutral or alkaline pH with the aid of an oxidizing agent which is added right at the time when the dyeing composition is employed or which is present in an oxidizing composition which is applied separately from the dye composition at the same time that said dye composition is applied to said fibers, or sequentially with the dye composition.

According to this embodiment of the dyeing process of the invention, the above-described dyeing composition is preferably mixed at the time of use with an oxidizing composition comprising, in a medium suitable for dyeing, at least one oxidizing agent which is present in an amount sufficient for color development. The resulting mixture is subsequently applied to the keratinous fibers and left to act for approximately 3 to 50 minutes, preferably for approximately 5 to 30 minutes, after which the fibers are rinsed, optionally washed with shampoo, rinsed again and dried.

The oxidizing agent present in the oxidizing composition as defined above can be chosen from the oxidizing agents conventionally used for the oxidation dyeing of keratinous fibers, among which preferred oxidizing agents are: hydrogen peroxide, urea hydrogen peroxide, alkali metal bromates, persalts, such as perborates and persulphates, and enzymes, such as peroxidases and oxidoreductases with 2 unpaired electrons. It is particularly preferred to use hydrogen peroxide.

The pH of the oxidizing composition comprising the oxidizing agent as defined above is such that, after it has been mixed with the dyeing composition, the pH of the resulting composition, applied to the keratinous fibers, preferably ranges from approximately 3 to 12, and more preferably from 5 to 11. The pH can be adjusted to the desired value by means of acidifying or basifying agents which are commonly used in dyeing keratinous fibers and are as defined above.

The oxidizing composition as defined above can also contain various adjuvants which are conventionally employed in hair-dyeing compositions and are as defined above.

The composition which is ultimately applied to the keratinous fibers can be in various forms, such as in the form of liquids, creams or gels, or in any other form suitable for dyeing keratinous fibers, and in particular human hair.

Another aspect of the invention is a multi-compartment device or "kit" or any other multi-compartment packaging system, a first compartment of which contains the dyeing composition as defined above and a second compartment of which contains the oxidizing composition as defined above. These devices may be equipped with a means for delivering the desired mixture onto the hair, such as the devices described in Patent FR-2,586,913 the disclosure of which is specifically incorporated by reference herein.

Certain compounds of formula (I), which are used as an oxidation base within the scope of the invention are novel and, to that extent, are further provided by the invention.

These novel compounds of formula (I') and the acid addition salts thereof correspond to the following formulae (I'a) to (I'f):

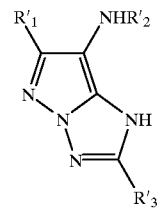 (I'a)

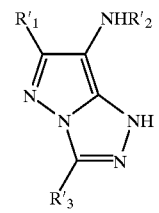 (I'b)

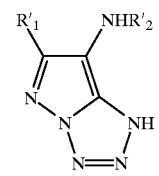 (I'c)

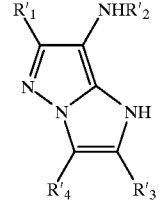 (I'd)

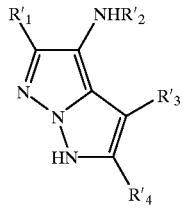 (I'e)

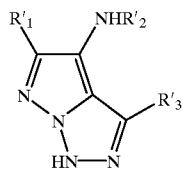 (I'f)

in which $R'_1$, $R'_2$, $R'_3$ and $R'_4$ have the same meanings as those indicated above for $R_1$, $R_2$, $R_3$ and $R_4$ of formula (I); it being understood that:

in the compounds of formula (I'b):
  i) when $R'_1$ represents a methyl radical and when $R'_2$ represents a hydrogen atom, then $R'_3$ is other than a methyl radical or than a $(CH_2)_3$—$SO_2$—$(CH_2)_{15}$—$CH_3$ or $CH(CH_3)$—$CH_2$—$SO_2$—$(CH_2)_{11}$—$CH_3$ radical;
  ii) when $R'_1$ represents a tert-butyl radical and when $R'_2$ represents a hydrogen atom, then $R'_3$ is other than a $(CH_2)_3$—$SO_2$—$(CH_2)_{11}$—$CH_3$ radical;

in the compounds of formula (I'd):
  when $R'_3$ and $R'_4$ together form a benzene radical and when $R'_2$ represents a hydrogen atom, then $R'_1$ is other than a methyl, —$CONH_2$ or carboxyl radical;
  when $R'_3$ and $R'_4$ together form a benzene radical substituted by a sulphonyl radical in the 4 position and when $R'_2$ represents a hydrogen atom, then $R'_1$ is other than a phenyl radical, a —$(CH_2)_{16}$—$CH_3$ radical or a —COOH radical;
  when $R'_3$ and $R'_4$ together form a benzene radical substituted by a carboxyl radical in the 4 position and when $R'_2$ represents a hydrogen atom, then $R'_1$ is other than a carboxyl radical.

The various compounds excluded by the above reservations are known in the photographic field or as analytical reagents (see in particular JP 02188748, JP 63074055, JP 61160745 and JP 60172982).

Preferred novel compounds of formula (I'a) above, are:
7-amino-2-methylpyrazolo[1,5-b]-1,2,4-triazole;
7-amino-2-ethylpyrazolo[1,5-b]-1,2,4-triazole;
7-amino-2-isopropylpyrazolo[1,5-b]-1,2,4-triazole;
7-amino-2-phenylpyrazolo[1,5-b]-1,2,4-triazole;
7-amino-2,6-dimethylpyrazolo[1,5-b]-1,2,4-triazole;
7-amino-6-methyl-2-ethylpyrazolo[1,5-b]-1,2,4triazole;
7-amino-6-methyl-2-isopropylpyrazolo[1,5-b]-1,2,4-triazole;
7-amino-6-methyl-2-phenylpyrazolo[1,5-b]-1,2,4-triazole;
7-amino-6-carboxy-2-methylpyrazolo[1,5-b]-1,2,4-triazole;
7-amino-6-carboxy-2-ethylpyrazolo[1,5-b]-1,2,4-triazole;
7-amino-6-carboxy-2-isopropylpyrazolo[1,5-b]-1,2,4-triazole;
7-amino-6-carboxy-2-phenylpyrazolo[1,5-b]-1,2,4-triazole;
7-amino-6-phenyl-2-methylpyrazolo[1,5-b]-1,2,4-triazole;
7-amino-6-phenyl-2-ethylpyrazolo[1,5-b]-1,2,4-triazole;
7-amino-6-phenyl-2-isopropylpyrazolo[1,5-b]-1,2,4-triazole;
6,7-diamino-2-methylpyrazolo[1,5-b]-1,2,4-triazole;
6,7-diamino-2-ethylpyrazolo[1,5-b]-1,2,4-triazole;
6,7-diamino-2-isopropylpyrazolo[1,5-b]-1,2,4-triazole;
6,7-diamino-2-phenylpyrazolo[1,5-b]-1,2,4-triazole;
7-amino-6-ethylthio-2-methylpyrazolo[1,5-b]-1,2,4-triazole;
7-amino-6-ethylthio-2-ethylpyrazolo[1,5-b]-1,2,4-triazole;
7-amino-6-ethylthio-2-isopropylpyrazolo[1,5-b]-1,2,4-triazole;
7-amino-6-ethylthio-2-phenylpyrazolo[1,5-b]-1,2,4-triazole;
7-amino-6-ethoxy-2-methylpyrazolo[1,5-b]-1,2,4-triazole;
7-amino-6-ethoxy-2-ethylpyrazolo[1,5-b]-1,2,4-triazole;
7-amino-6-ethoxy-2-isopropylpyrazolo[1,5-b]-1,2,4-triazole;
7-amino-6-ethoxy-2-phenylpyrazolo[1,5-b]-1,2,4-triazole;
7-amino-6-methyl-2-(2'-aminoethyl)pyrazolo[1,5-b]-1,2,4-triazole;
7-amino-6-carboxy-2-(2'-aminoethyl)pyrazolo[1,5-b]-1,2,4-triazole;
7-amino-6-phenyl-2-(2'-aminoethyl)pyrazolo[1,5-b]-1,2,4-triazole;
7-amino-6-ethylthio-2-(2'-aminoethyl)pyrazolo[1,5-b]-1,2,4-triazole;
7-amino-2-(2'-aminoethyl)pyrazolo[1,5-b]-1,2,4-triazole;
7-amino-2-(2'-hydroxyethyl)pyrazolo[1,5-b]-1,2,4-triazole;
7-amino-6-methyl-2-(2'-hydroxyethyl)pyrazolo[1,5-b]-1,2,4-triazole;
7-amino-6-ethylthio-2-(2'-hydroxyethyl)pyrazolo[1,5-b]-1,2,4-triazole;
7-amino-6-carboxy-2-(2'-hydroxyethyl)pyrazolo[1,5-b-1,2,4-triazole;

7-amino-6-phenyl-2-(2'-hydroxyethyl)pyrazolo[1,5-b]-1,2,4-triazole;
6,7-diamino-2-(2'-aminoethyl)pyrazolo[1,5-b]-1,2,4-triazole;
6,7-diamino-2-(2'-hydroxyethyl)pyrazolo[1,5-b]-1,2,4-triazole;
7-amino-6-ethoxy-2-(2'-aminoethyl)pyrazolo[1,5-b]-1,2,4-triazole;
7-amino-6-ethoxy-2-(2'-hydroxyethyl)pyrazolo[1,5-b-]1,2,4-triazole;
and the acid addition salts thereof.

Preferred novel compounds of formula (I'b), are:
7-amino-3-methylpyrazolo[3,2-c]-1,2,4-triazole;
7-amino-3-ethylpyrazolo[3,2-c]-1,2,4-triazole;
7-amino-3-isopropylpyrazolo[3,2-c]-1,2,4-triazole;
7-amino-3-phenylpyrazolo[3,2-c]-1,2,4-triazole;
7-amino-3-(2'-aminoethyl)pyrazolo[3,2-c]-1,2,4-triazole;
7-amino-3-(2'-hydroxyethyl)pyrazolo[3,2-c]-1,2,4-triazole;
7-amino-6-methyl-3-ethylpyrazolo[3,2-c]-1,2,4-triazole;
7-amino-3,6-dimethylpyrazolo[3,2-c]-1,2,4-triazole;
7-amino-6-methyl-3-isopropylpyrazolo[3,2-c]-1,2,4-triazole;
7-amino-6-methyl-3-phenylpyrazolo[3,2-c]-1,2,4-triazole;
7-amino-6-methyl-3-(2'-aminoethyl)pyrazolo[3,2-c]-1,2,4-triazole;
7-amino-6-methyl-3-(2'-hydroxyethyl)pyrazolo[3,2-c]-1,2,4-triazole;
7-amino-6-methyl-3-(methylthio)pyrazolo[3,2-c]-1,2,4-triazole;
7-amino-6-phenyl-3-methylpyrazolo[3,2-c]-1,2,4-triazole;
7-amino-6-phenyl-3-ethylpyrazolo[3,2-c]-1,2,4-triazole;
7-amino-6-phenyl-3-isopropylpyrazolo[3,2-c]-1,2,4-triazole;
7-amino-6-phenyl-3-phenylpyrazolo[3,2-c]-1,2,4-triazole;
7-amino-6-phenyl-3-(2'-aminoethyl)pyrazolo[3,2-c]-1,2,4-triazole;
7-amino-6-phenyl-3-(2'-hydroxyethyl)pyrazolo[3,2-c]-1,2,4-triazole;
7-amino-6-phenyl-3-(methylthio)pyrazolo[3,2-c]-1,2,4-triazole;
7-amino-6-ethylthio-3-methylpyrazolo[3,2-c]-1,2,4-triazole;
7-amino-6-ethylthio-3-ethylpyrazolo[3,2-c]-1,2,4-triazole;
7-amino-6-ethylthio-3-isopropylpyrazolo[3,2-c]-1,2,4-triazole;
7-amino-6-ethylthio-3-phenylpyrazolo[3,2-c]-1,2,4-triazole;
7-amino-6-ethylthio-3-(2'-aminoethyl)pyrazolo[3,2-c]-1,2,4-triazole;
7-amino-6-ethylthio-3-(2'-hydroxyethyl)pyrazolo[3,2-c]-1,2,4-triazole;
7-amino-6-trifluoromethyl-3-(methylthio)pyrazolo[3,2-c]-1,2,4-triazole;
7-amino-6-(trifluoromethyl)pyrazolo[3,2-c]-1,2,4-triazole;
7-amino-6-carboxy-3-methylpyrazolo[3,2-c]-1,2,4-triazole;
7-amino-6-carboxy-3-ethylpyrazolo[3,2-c]-1,2,4-triazole;
7-amino-6-carboxy-3-isopropylpyrazolo[3,2-c]-1,2,4-triazole;
7-amino-6-carboxy-3-phenylpyrazolo[3,2-c]-1,2,4-triazole;
7-amino-6-carboxy-3-(2'-aminoethyl)pyrazolo[3,2-c]-1,2,4-triazole;
7-amino-6-carboxy-3-(2'-hydroxyethyl)pyrazolo[3,2-c]-1,2,4-triazole;
6,7-diamino-3-methylpyrazolo[3,2-c]-1,2,4-triazole;
6,7-diamino-3-ethylpyrazolo[3,2-c]-1,2,4-triazole;
6,7-diamino-3-phenylpyrazolo[3,2-c]-1,2,4-triazole;
6,7-diamino-3-isopropylpyrazolo[3,2-c]-1,2,4-triazole;
7-amino-6-ethoxy-3-methylpyrazolo[3,2-c]-1,2,4-triazole;
7-amino-6-ethoxy-3-ethylpyrazolo[3,2-c]-1,2,4-triazole;
7-amino-6-ethoxy-3-isopropylpyrazolo[3,2-c]-1,2,4-triazole;
7-amino-6-ethoxy-3-phenylpyrazolo[3,2-c]-1,2,4-triazole;
7-amino-6-ethoxy-3-(2'-aminoethyl)pyrazolo[3,2-c]-1,2,4-triazole;
7-amino-6-ethoxy-3-(2'-hydroxyethyl)pyrazolo[3,2-c]-1,2,4-triazole;
6,7-diamino-3-(2'-aminoethyl)pyrazolo[3,2-c]-1,2,4-triazole;
6,7-diamino-3-(2'-hydroxyethyl)pyrazolo[3,2-c]-1,2,4-triazole;
and the acid addition salts thereof.

Preferred novel compounds of formula (I'c), are:
7-amino-6-methylpyrazolo[5,1-e]tetrazole;
7-amino-6-phenylpyrazolo[5,1-e]tetrazole;
7-amino-6-carboxypyrazolo[5,1-e]tetrazole;
and the acid addition salts thereof.

Preferred novel compounds of formula (I'd), are:
7-aminopyrazolo[1,5-a]imidazole;
7-amino-2-methylpyrazolo[1,5-a]imidazole;
7-amino-2-phenylpyrazolo[1,5-a]imidazole;
7-aminopyrazolo[1,5-a]benzimidazole;
7-amino-6-methylpyrazolo[1,5-a]imidazole;
7-amino-2,6-dimethylpyrazolo[1,5-a]imidazole;
7-amino-6-methyl-2-phenylpyrazolo[1,5-a]imidazole;
7-amino-6-phenylpyrazolo[1,5-a]imidazole;
7-amino-6-phenyl-2-methylpyrazolo[1,5-a]imidazole;
7-amino-2,6-diphenylpyrazolo[1,5-a]imidazole;
7-amino-6-phenylpyrazolo[1,5-a]benzimidazole;
7-amino-6-carboxypyrazolo[1,5-a]imidazole;
7-amino-6-carboxy-2-methylpyrazolo[1,5-a]imidazole;
7-amino-6-carboxy-2-phenylpyrazolo[1,5-a]imidazole;
7-amino-6-ethoxypyrazolo[1,5-a]imidazole;
7-amino-6-ethoxy-2-methylpyrazolo[1,5-a]imidazole;
7-amino-6-ethoxy-2-phenylpyrazolo[1,5-a]imidazole;
7-amino-6-ethoxypyrazolo[1,5-a]benzimidazole;
7-amino-6-(trifluoromethyl)pyrazolo[1,5-a]benzimidazole;
7-amino-6-aminopyrazolo[1,5-a]imidazole;
7-amino-6-amino-2-methylpyrazolo[1,5-a]imidazole;
7-amino-6-amino-2-phenylpyrazolo[1,5-a]imidazole;
7-amino-6-aminopyrazolo[1,5-a]benzimidazole;
7-amino-6-(ethylthio)pyrazolo[1,5-a]imidazole;
7-amino-6-ethylthio-2-methylpyrazolo[1,5-a]imidazole;
7-amino-6-ethylthio-2-phenylpyrazolo[1,5-a]imidazole;
7-amino-6-methyl-2-hydroxypyrazolo[1,5-a]imidazole;
7-amino-6-phenyl-2-hydroxypyrazolo[1,5-a]imidazole;
7-amino-6-ethoxy-2-hydroxypyrazolo[1,5-a]imidazole;
7-amino-6-ethylthio-2-hydroxypyrazolo[1,5-a]imidazole;
6,7-diamino-2-hydroxypyrazolo[1,5-a]imidazole;
and the acid addition salts thereof.

Preferred novel compounds of formula (I'e), are:
5,8-diamino-4-methylpyrazolo[5,1-e]pyrazole;
5,7,8-triamino-4-methylpyrazolo[5,1-e]pyrazole;
and the acid addition salts thereof.

Preferred novel compounds of formula (I'f), are:
6-amino-5-methylpyrazolo[5,1-e]-1,2,3-triazole;
6-amino-5-phenylpyrazolo[5,1-e]-1,2,3-triazole;
and the acid addition salts thereof.

The novel compounds of formula (I') in accordance with the present invention can be prepared according to the methods described in the following patent applications and patents: FR 2,075,583, EP-A-119,860, EP-A-285,274, EP-A-244,160, EP-A-578,248, GB 1,458,377, U.S. Pat. Nos. 3,227,554, 3,419,391, 3,061,432, 4,500,630, 3,725,067, 3,926,631, 5,457,210, JP 84/99437, JP 83/42045, JP 84/162548, JP 84/171956, JP 85/33552, JP 85/43659, JP 85/172982, JP 85/190779, JP 41/33053, EP 433,854, JP 62/129851 JP 60/140241, as well as in the following publications:

Chem. Ber., 32, 797 (1899), Chem. Ber., 89, 2550 (1956),
J. Chem. Soc. Perkin Trans. I, 2047 (1977),
J. Prakt. Chem., 320, 533 (1978).

The following examples are intended to illustrate the invention, without, however, limiting its scope.

PREPARATION EXAMPLES

Preparation Example A

Synthesis of 1H-7-amino-2,6-dimethylpyrazolo[1,5-b]-1,2,4-triazole hydrochloride

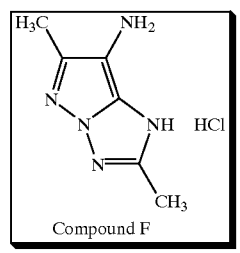
Compound F

Synthetic scheme

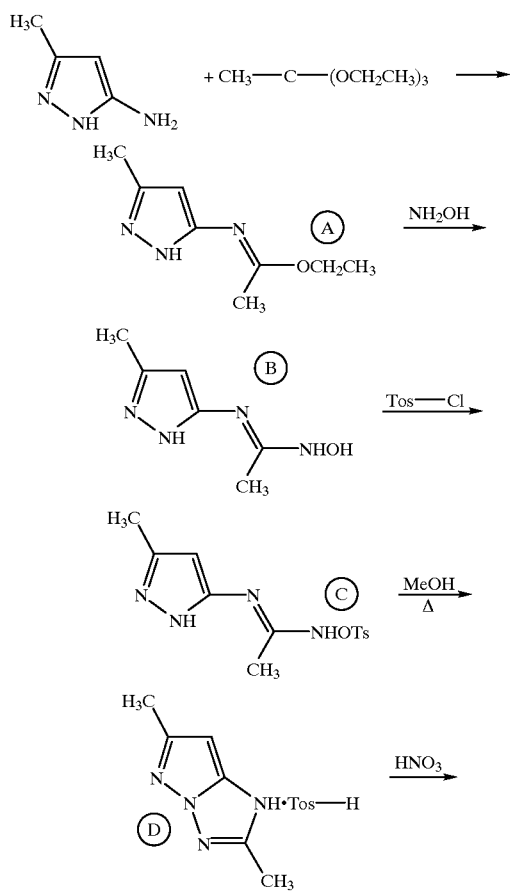

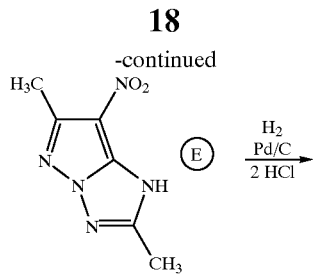

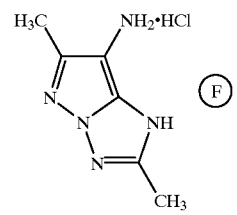

200 g (1.23 mol) of ethyl orthoacetate were added over 20 minutes at room temperature to a solution of 100 g of 5-amino-3-methylpyrazole (1.03 mol) in 500 cm³ of diglyme. The reaction mixture was heated at 95° C. and then concentrated at 55° C. under 300 Pa, in order to obtain 164 g of an orange oil corresponding to product A.

180 cm³ of a sodium methoxide solution (5.7M in methanol) were added at room temperature to a solution of 71.7 g (1.03 mol) of hydroxylamine hydrochloride in 1.5 l of absolute ethanol. After stirring for 30 minutes, the reaction mixture was cooled to 5° C. and filtered. The salts were washed 2 times with 100 cm³ of absolute ethanol and the two ethanol washes were combined. 164 g (0.98 mol) of compound A, prepared as above, dissolved in 150 cm³ of ethanol, were added to this solution at a temperature of 50° C.

The reaction mixture was allowed to warm up again to room temperature and stirred for an additional 1 h. The reaction mixture was then cooled to 5° C. and the precipitate obtained was filtered off, washed with 2 times 100 cm³ of isopropyl ether and dried at 50° C. under 5300 Pa. 52 g of a first crop of white solid were thus obtained, which solid corresponds to the compound B, the melting point of which was 197° C.

The ethanol filtrate and the ether washes were combined and then concentrated to dryness before being titrated in 300 cm³ of tetrahydrofuran. This second precipitate was filtered, washed with isopropyl ether and dried at 50° C. under vacuum to yield 16 g of a second crop of white precipitate with a melting point of 197° C. corresponding to the compound B.

20.05 cm³ (0.143 mol) of anhydrous triethylamine and 27.2 g (0.143 mol) of the acid chloride of para-toluenesulphonic acid were added to a solution of 20 g (0.13 mol) of compound B, prepared above, in 9.5 liters of anhydrous tetrahydrofuran. The reaction mixture was stirred for 2 hours at room temperature and then cooled to 0° C. The triethylamine hydrochloride was separated by filtration and the filtrate was concentrated under a vacuum of 8 kPa at approximately 50° C. until the beginning of crystallization. Cooling was carried out to 0° C. and the precipitate was filtered off on a sintered glass, washed with ice-cold tetrahydrofuran and then dried under vacuum at a temperature of 40° C. 38.2 g of compound C were thus obtained in the form of a white solid, the melting point of which was between 105° C. and 128° C. (decomposition).

A solution of 35 g (0.113 mol) of compound C obtained above in 1 liter of methanol was heated at reflux for 2 hours and then the solution was evaporated to dryness. An oil was obtained which crystallized when 100 cm³ of isopropyl ether were added. The crystals were filtered off on a sintered glass and then recrystallized from a mixture of isopropanol and heptane. After drying under a vacuum at 40° C., 19 g of 1H-2,6-dimethylpyrazolo[1,5-b]-1,2,4-triazole tosylate (compound D) were obtained in the form of a white solid, the melting point of which was 157° C.

8.9 cm³ of fuming nitric acid were added, taking care not to exceed a temperature of 5° C., to a solution of 19 g (0.062 mol) of compound D in 35 cm³ of concentrated sulphuric acid at a temperature ranging from 0° C. to 5° C. The reaction mixture was subsequently heated to room temperature, stirred for 4 hours and then slowly poured onto 400 g of crushed ice. The white solid which precipitated was filtered off, washed 2 times with 15 cm³ of ice-cold water and dried at 40° C. under vacuum. 8.5 g of white solid, which corresponds to compound E with a melting point of 273° C., were thus obtained.

1.4 g of 5% by weight palladium-on-charcoal comprising 50% water were added to a solution of 8 g (0.044 mol) of compound E in 300 cm³ of methanol. The suspension was placed in a hydrogenator under a pressure of 13 bar of hydrogen and at a temperature of 70° C. for 5 hours. The contents of the hydrogenator were withdrawn and filtered on a sintered glass. The filtrate was subsequently added to 100 cm³ of a 4M ethanolic hydrochloric acid solution. 350 cm³ of ethyl ether were added to this solution and the precipitate that formed was filtered off, washed twice with 20 cm³ of ethyl ether and dried at 40° C. under vacuum to produce 7.2 g of beige solid corresponding to compound F with a melting point of 213° C.

The elemental analysis for $C_6H_9N_5 \cdot HCl$ was:

| % | C | H | N | Cl |
|---|---|---|---|---|
| Calculated | 38.41 | 5.37 | 37.32 | 18.89 |
| Found | 38.22 | 5.14 | 36.57 | 19.03 |

Preparation Example B

Synthesis of 1H-7-amino-3,6-dimethylpyrazolo[3,2-c]-1,2,4-triazole dihydrochloride

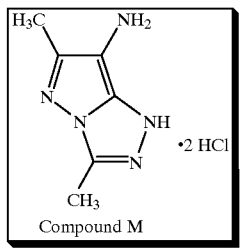
Compound M

Synthetic scheme

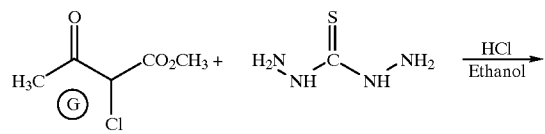

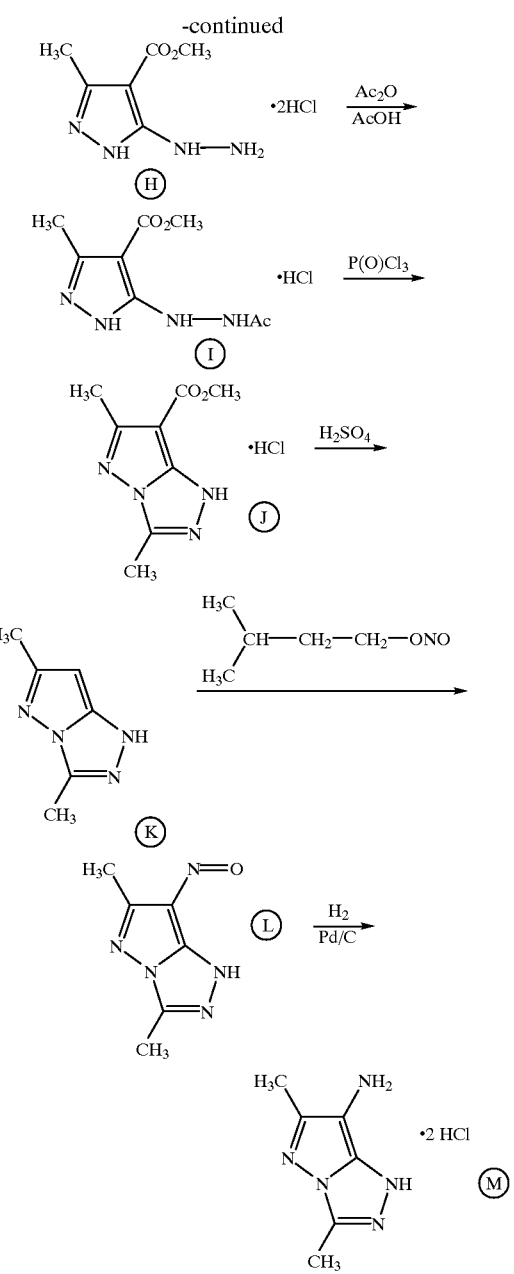

113.5 g (0.754 mol) of methyl 2-chloroacetoacetate (compound G) were added at a temperature of 80° C. to a solution of 80 g of thiocarbazide (0.754 mol) in 2 liters of ethanol and 700 cm³ of 12N hydrochloric acid. The reaction mixture was heated at reflux for 1 hour and then cooled to 0° C. The solid that formed was filtered off, washed twice with 200 cm³ of isopropyl ether and then dried at 40° C. under vacuum. The solid was then dissolved in 800 cm³ of methanol at reflux and the solution was cooled to 0° C. The solid thus formed was filtered off, washed twice with 100 cm³ of isopropyl ether and dried at 40° C. under vacuum. 12.65 g of beige powder, which corresponds to compound H and has a melting point of 199° C., were thus obtained.

The recrystallized filtrate was concentrated by half and 700 cm³ of isopropyl ether were added to this concentrate. The solid thus formed was filtered off, washed twice with 100 cm³ of isopropyl ether and dried at 40° C. under vacuum. 9.14 g of beige solid, which corresponds to compound H and has a melting point of 200° C., were thus obtained. The same protocol was followed on the latter filtrate and 6.9 g of a beige solid were obtained, which corresponds to compound H with a melting point of 199° C.

9.7 cm³ of acetic anhydride were added to a suspension of 25 g (0.103 mol) of compound H in 750 cm³ of acetic acid. The reaction mixture was heated at reflux for 1 hour and then cooled to 16° C. The white precipitate was then filtered off, washed with 250 cm³ of diisopropyl ether and dried at 40° C. under vacuum. 19 g of white solid, which corresponds to compound I and has a melting point of 216° C., were thus obtained. The filtrate was concentrated to a volume of approximately 30 cm³ and then cooled to 16° C. 15 cm³ of acetone and 45 cm³ of isopropyl ether were added to this solution. The precipitate was then filtered off, washed twice with 50 cm³ of isopropyl ether and dried at 40° C. under vacuum. 4.7 g of a second crop of white precipitate, which corresponds to compound I and has a melting point of 216° C., were thus obtained.

22 cm³ of phosphoryl chloride were added at room temperature and with vigorous stirring to a suspension of 23 g of compound I (0.092 mol) in 1.2 liters of toluene. The reaction mixture was heated at reflux for 5 hours and then cooled to 0C. The precipitate obtained was filtered off, washed twice with 200 cm³ of heptane and dried under a pressure of 40 mm of mercury at 40° C. 11 g of yellow precipitate were thus obtained and were recrystallized from 30 cm³ of absolute ethanol, in order to yield 5 g of yellow powder corresponding to compound J with a melting point of 192° C.

1.7 cm³ of 10N sodium hydroxide solution were added at a temperature of 5° C. to a solution of 3.8 g (0.016 mol) of compound J in 20 cm³ of water. 60 cm³ of 98% concentrated sulphuric acid were added to this solution, taking care that the temperature remained between 7 and 10° C. The reaction mixture was subsequently heated at 100° C.–120° C. for 1 h 30. After cooling to 0° C., the reaction mixture was poured into 200 g of ice and its pH was adjusted to pH 8 using 10N sodium hydroxide solution, taking care that the temperature did not exceed 10° C.

The aqueous phase was subsequently extracted 3 times with 300 cm³ of ethyl acetate. The organic phase was dried over sodium sulphate and concentrated to a volume of approximately 30 cm³. The yellow precipitate obtained was filtered off, washed twice with 50 cm³ of heptane and dried at 40° C. under vacuum. 1.2 g of yellow powder, which corresponds to compound K and has a melting point of 118° C., were thus obtained.

4N hydrochloric acid was added to a solution of 1 g of compound K (7.3 mmol) in 20 cm³ of isopropanol and 20 cm³ of absolute ethanol until the pH of the solution was 5. The reaction mixture was cooled to 5° C. and 1 cm³ of isopentyl nitrite was added thereto. The temperature of the reaction mixture was brought to 25° C. After stirring for 1 hour, the reaction mixture was cooled to 0° C. and the precipitate was filtered off, washed with diisopropyl ether and dried at 30° C. under vacuum. 1.2 g of beige solid, which corresponds to compound L and has a melting point of 210° C., were thus obtained.

0.4 g of 5% by weight palladium-on-charcoal comprising 50% water was added to a solution of 1 g (6 mmol) of compound L in 200 cm³ of methanol. The suspension was placed in a hydrogenator under a pressure of 3.5 bar of hydrogen at 30° C. for 1 hour. The contents of the hydrogenator were subsequently removed and filtered. The filtrate was run into a solution comprising 200 cm³ of diisopropyl ether and 10 cm³ of 5M ethanolic hydrochloric acid solution. The precipitate formed was filtered off, washed with diisopropyl ether and dried at 40° C. under vacuum. 0.9 g of light beige powder, which corresponds to compound M and has a melting point of 206° C., was thus obtained and was named, with the numbering conventions defined above, 7-amino-3,6-dimethylpyrazolo[3,2-c]-1,2,4-triazole dihydrochloride.

| The elemental analysis for $C_6H_9N_5.2HCl.H_2O$ was: | | | | |
|---|---|---|---|---|
| % | C | H | N | Cl |
| Calculated | 29.77 | 5.41 | 28.93 | 29.29 |
| Found | 29.07 | 5.19 | 28.04 | 29.48 |

Preparation Example C

Synthesis of 1H-7-amino-6-methylpyrazolo[1,5-a] imidazole dihydrochloride

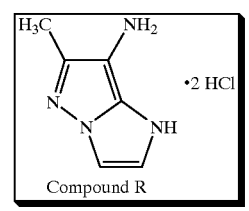

Compound R

Synthetic scheme

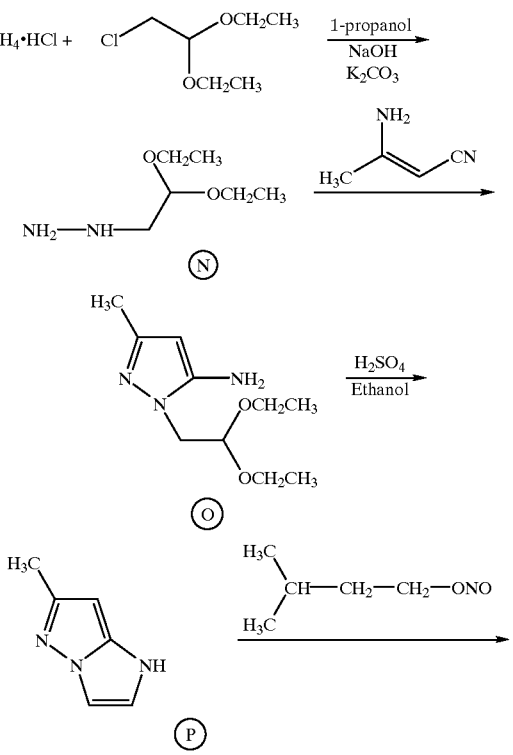

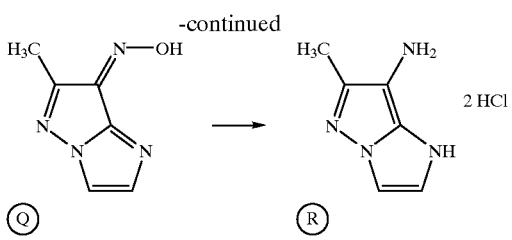

685 g of hydrazine hydrochloride (10 mol) were added to a solution of 410 g of sodium hydroxide in 6 liters of n-propanol at 25° C. After stirring for 1 hour, 452 g of potassium carbonate (3.27 mol) were introduced at room temperature, followed by 1 kg of chloroacetaldehyde diethyl acetal. The reaction mixture was heated at boiling point for 40 hours and then cooled to 5° C. The precipitated salts were filtered off and washed twice with 200 cm³ of absolute ethanol. The combined filtrate and ethanolic phase were concentrated until a yellow oil was obtained, which oil was distilled under a pressure of 1.3 Pa at a temperature of 78–82° C. 446 g of colorless oil, which corresponds to compound N, were thus isolated.

14.8 g (0.1 mol) of compound N, diluted beforehand in 20 cm³ of n-pentanol, were added at 25° C. to a solution of 8.2 g (0.1 mol) of 3-aminocrotononitrile in 100 cm³ of n-pentanol. The reaction mixture was heated at reflux for 5 hours and then concentrated to distil off the n-pentanol under a pressure of 5.3 kPa. The brown oil which was obtained was subsequently distilled under a vacuum of 3 Pa at a temperature of 117–119° C., in order to isolate a pale yellow oil. 17.8 g of oil, which corresponds to compound O, were thus obtained.

200 cm³ of 20% aqueous sulphuric acid were added at room temperature to a solution of 17 g (0.08 mol) of compound O in 300 cm³ of absolute ethanol. The reaction mixture was subsequently heated at reflux for 3 hours and then cooled to 50° C. The pH of the reaction mixture was adjusted to pH 8 using a saturated solution of sodium hydrogencarbonate in water. The sodium sulphate salt was filtered from the reaction mixture and the filtrate was concentrated, to remove the ethanol. The aqueous phase thus obtained was extracted 3 times with 300 cm³ of ethyl acetate and then with 300 cm³ of an ethyl acetate/methanol mixture in the proportions of 90/10. The combined organic phases were dried over magnesium sulphate and then concentrated to dryness. The orange solid obtained was subsequently triturated in 200 cm³ of heptane, filtered off and washed with 50 cm³ of heptane, and then dried at 40° C. under vacuum. 9.8 g of orange solid, which corresponds to compound P and has a melting point of 138° C., were thus obtained.

12N hydrochloric acid was added to a solution of 2 g (0.016 mol) of compound P in 10 cm³ of absolute ethanol at 5° C. until the reaction mixture reached a pH of 5–6. 2.2 cm³ (0.016 mol) of isoamyl nitrite were then added to this solution at 5° C. and the temperature of the reaction mixture was gradually increased to approximately 20° C. After stirring for 1 hour, the suspension was cooled to 5° C. and the precipitate was filtered off, washed twice with 20 cm³ of heptane and dried at 35° C. under vacuum. 1.4 g of red-brown solid, which corresponds to compound Q and has a melting point of 216° C., were thus obtained.

0.3 g of 5% palladium-on-charcoal comprising 50% water was added to a solution of 1 g (6.66 mmol) of compound Q in 150 cm³ of methanol. The suspension was placed in a hydrogenator under a pressure of 1.5 bar at 30° C. for 1 h 30.

The contents of the hydrogenator were subsequently withdrawn and filtered. The filtrate was run into a solution comprising 100 cm³ of isopropyl alcohol and 10 cm³ of 5M ethanolic hydrochloric acid. The solution was concentrated to a volume corresponding to the volume used at beginning of the crystallization of the reduced product. The suspension was then cooled to ice-cold temperatures, and the precipitate was filtered off, washed with ice-cold isopropanol and dried at 40° C. under vacuum. 0.55 g of light beige solid, which corresponds to compound R and has a decomposition point between 230° and 250° C., was thus obtained and was named, with the numbering conventions defined above, 7-amino-6-methylpyrazolo[1,5-a]imidazole dihydrochloride.

| The elemental analysis for $C_6H_8N_4 \cdot 2HCl$ was: | | | | |
|---|---|---|---|---|
| % | C | H | N | Cl |
| Calculated | 34.47 | 4.82 | 26.80 | 33.91 |
| Found | 33.99 | 4.84 | 25.69 | 35.08 |

Dyeing Examples

Example 1 of Dyeing in Alkaline Medium

| The following dyeing composition was prepared: | |
|---|---|
| 7-amino-3,6-dimethylpyrazolo[3,2-c]-1,2,4-triazole dihydrochloride monohydrate (compound of formula (I)) | 0.672 g |
| Resorcin | 0.330 g |
| Benzyl alcohol | 2 g |
| Polyethylene glycol with 6 mol of ethylene oxide | 3 g |
| Ethanol | 18 g |
| ($C_8$–$C_{10}$) alkyl polyglucoside as a 60% aqueous solution of active material buffered with ammonium citrate, sold under the name ORAMIX CG110 ® by Seppic | 6 g |
| Aqueous ammonia comprising 20% of $NH_3$ | 10 g |
| Sodium metabisulphite | 0.208 g |
| Sequestering agent | q.s. |
| Demineralized water | q.s. for 100 g |

At the time of use, the above dyeing composition was mixed weight for weight with an oxidizing composition composed of an aqueous solution comprising $6 \times 10^{-}$mol % of ammonium persulphate. The mixture obtained exhibited a pH of approximately 9.7 and was applied to locks of natural grey hair containing 90% of white hairs for 30 minutes. The hair was subsequently rinsed, washed with a standard shampoo and dried.

The hair was dyed in an ash iridescent shade.

Examples 2 and 3 of Dyeing in Alkaline Medium

| The following dyeing compositions were prepared (contents in grams): | | |
|---|---|---|
| EXAMPLE | 2 | 3 |
| 7-Amino-6-methylpyrazolo[1,5-a]benzimidazole.2HCl (Compound of formula (I)) | 1.43 | — |

-continued

The following dyeing compositions were prepared (contents in grams):

| EXAMPLE | 2 | 3 |
|---|---|---|
| 7-Amino-3,6-dimethylpyrazolo[3,2-c]-1,2,4-triazole.2HCl.H$_2$O (Compound of formula (I)) | — | 1.12 |
| Common dyeing vehicle No. 1 | (*) | (*) |
| Demineralized water, q.s. for | 100 g | 100 g |

| (*) Common dyeing vehicle No. 1: | |
|---|---|
| Benzyl alcohol | 3 g |
| Polyethylene glycol with 6 mol of ethylene oxide | 4.5 g |
| Ethanol | 15 g |
| (C$_8$–C$_{10}$) alkyl polyglucoside as a 60% aqueous solution of active material buffered with ammonium citrate, sold under the name ORAMIX CG1100 ® by Seppic | 9 g |
| Ammoniacal buffer (1M NH$_4$OH/1M NH$_4$Cl) | 24 g |

These compositions had a pH of approximately 9.5 and were applied to locks of natural grey hair containing 90% of white hairs for 30 minutes. The coloring developed without any other oxidizing agent than atmospheric oxygen. The hair was subsequently rinsed, washed with a standard shampoo and dried.

The hair was dyed in a shade which appears in the table below:

| EXAMPLE | SHADE OBTAINED |
|---|---|
| 2 | Toned-down iridescent red |
| 3 | Coppery golden |

Example 4 of Dyeing in Neutral Medium

The following dyeing composition prepared:

| | |
|---|---|
| 7-Amino-3,6-dimethylpyrazolo[3,2-c]-1,2,4-triazole.2HCl.H$_2$O (compound of formula (I)) | 1.12 g |
| Benzyl alcohol | 3 g |
| Polyethylene glycol with 6 mol of ethylene oxide | 4.5 g |
| Ethanol | 15 g |
| (C$_8$–C$_{10}$) alkyl polyglucoside as a 60% aqueous solution of active material buffered with ammonium citrate, sold under the name ORAMIX CG110 ® by Seppic | 9 g |
| Phosphate buffer (1.5M K$_2$HPO$_4$/1M KH$_2$PO$_4$) | 24 g |
| Demineralized water | q.s. for 100 g |

This composition had a pH of approximately 7 and was applied to locks of natural grey hair containing 90% of white hairs for 30 minutes. The coloring developed without any other oxidizing agent than atmospheric oxygen. The hair was subsequently rinsed, washed with a standard shampoo and dried.

The hair was dyed in a golden coppery shade.

EXAMPLES 5 and 6 of Dyeing in Alkaline Medium

The following dyeing compositions were prepared (contents in grams):

| EXAMPLE | 5 | 6 |
|---|---|---|
| 7-Amino-2,6-dimethylpyrazolo[1,5-b]-1,2,4-triazole-HCl (Compound of formula (I)) | 0.726 | 0.726 |
| 2-Methyl-5-aminophenol (coupler) | 0.369 | — |
| meta-Aminophenol | — | 0.327 |
| Common dyeing vehicle No. 2 | () | () |
| Demineralized water, q.s. for | 100 g | 100 g |

| (**) Common dyeing vehicle No. 2: | |
|---|---|
| Ethanol | 30 g |
| Ammonium acetate | 0.8 g |
| Sodium metabisulphite as a 35% aqueous solution | 1.3 g |
| Aqueous ammonia comprising 20% of NH$_3$ | q.s. for pH 10 |

At the time of use, the dyeing composition of Example 5 was mixed weight for weight with a 20-volume hydrogen peroxide solution (6% by weight) with a pH of 3. The mixture obtained exhibited a pH of approximately 9.9.

At the time of use, the dyeing composition of Example 6 was mixed weight for weight with an aqueous solution comprising $6\times10^{-3}$ mol % of ammonium persulphate. The mixture obtained exhibited a pH of approximately 9.7.

Each of the mixtures obtained was applied for 30 minutes to locks of natural grey hair containing 90% of white hairs. The hair was subsequently rinsed, washed with a standard shampoo, rinsed again and then dried.

The hair was dyed in a shade which appears in the table below:

| EXAMPLE | SHADE OBTAINED |
|---|---|
| 5 | Salmon |
| 6 | Fuchsia |

Examples 7 to 12 of Dyeing in Acidic Medium

The following dyeing compositions were prepared (contents in grams):

| EXAMPLE | 7 | 8 | 9 | 10 | 11 | 12 |
|---|---|---|---|---|---|---|
| 7-Amino-2,6-dimethylpyrazolo[1,5-b]-1,2,4-triazole HCl (compound of formula (I)) | 0.726 | 0.726 | — | — | — | — |
| 1H-7-Aminopyrazolo[1,5-a]imidazole-2HCl (compound of formula (I)) | — | — | 0.585 | 0.585 | 0.585 | — |
| 1H-7-Amino-6-methylpyrazolo[1,5-a]imidazole-2HCl (compound of formula (I)) | — | — | — | — | — | 0.627 |
| 2,4-Diaminophenoxyethanol dihydrochloride (coupler) | 0.723 | — | 0.723 | — | 0.723 | 0.723 |
| 2-Methyl-5-aminophenol (coupler) | — | 0.369 | — | — | — | — |
| meta-Aminophenol (coupler) | — | — | — | 0.327 | — | — |
| Common dyeing vehicle No. 3 | (*) | (*) | (*) | (*) | (*) | (*) |
| Demineralized water, q.s. for | 100 g | 100 g | 100 g | 100 g | 100 g | 100 g |

| (***) Common dyeing vehicle No. 3: | |
|---|---|
| Ethanol | 20 g |
| $K_2HPO_4/KH_2PO_4$ (1.5M/1M) buffer | 10 g |
| Sodium metabisulphite as a 50% aqueous solution | 1.3 g |

At the time of use, the dyeing compositions of Examples 7, 8 and 10 to 12 were mixed weight for weight with a 20-volume hydrogen peroxide solution (6% by weight).

At the time of use, the dyeing composition of Example 9 was mixed weight for weight with an aqueous solution comprising $6 \times 10^{-3}$ mol % of ammonium persulphate.

Each of the mixtures obtained was applied for 30 minutes to locks of natural grey hair containing 90% of white hairs. The hair was subsequently rinsed, washed with a standard shampoo, rinsed again and then dried.

The hair was dyed in a shade which appears in the table below:

| EXAMPLE | Dyeing pH | Shade obtained |
|---|---|---|
| 7 | 6.4 ± 0.2 | Purple |
| 8 | 6.1 ± 0.2 | Pinkish orangey |
| 9 | 3.2 ± 0.2 | Purplish ash |
| 10 | 6.2 ± 0.2 | Coppery red |
| 11 | 5.5 ± 0.2 | Deep purple |
| 12 | 5.5 ± 0.2 | Deep purple |

What is claimed is:

1. A composition for the oxidation dyeing of keratinous fibers, wherein said composition comprises, in a medium suitable for dyeing:

as oxidation base, at least one pyrazoloazole compound of formula (I) or at least one acid addition salt thereof:

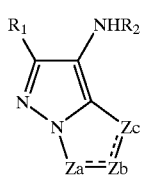

(I)

in which:

$R_1$ represents: a hydrogen atom; a linear or branched $C_1-C_{20}$ alkyl radical, optionally substituted by 1 or 2 radicals R chosen from a halogen atom, a $C_1-C_4$ alkyl radical, a trifluoromethyl radical, a carboxyl radical, an alkyldioxy radical, a nitro radical, a cyano radical, a hydroxyl radical, an alkoxy radical, an aryloxy radical, an amino radical, an alkylamino radical, an acylamino radical, a carbamoyl radical, a sulphonamido radical, a sulphamoyl radical, an imido radical, an alkylthio radical, an arylthio radical, an aryl radical, a $(C_1-C_4)$ alkoxy-carbonyl radical and an acyl radical; an aryl radical optionally substituted by 1 or 2 radicals R as defined above; a 5- or 6-membered heterocycle containing at least one nitrogen, oxygen or sulphur atom wherein said heterocycle is optionally substituted by 1 or 2 radicals R as defined above;

when $R_1$ denotes a $C_1-C_4$ alkyl radical, an aryl radical or a 5- or 6-membered heterocycle, it can be connected to the carbon atom of the pyrazole via an oxygen, nitrogen or sulphur atom;

$R_1$ can, additionally, denote a halogen atom; a trifluoromethyl radical; a 4-trifluoromethylphenyl ring: a $C_1-C_4$ monohydroxyalkyl radical; a $C_1-C_4$ aminoalkyl radical; a $(C_1-C_4)$alkylamino$(C_1-C_4)$alkyl radical; a $C_1-C_4$ alkoxy radical; an aryloxy radical; a $C_1-C_4$ alkylthio radical; an arylthio radical; a $C_1-C_4$ alkylsulphonyl radical; an acyl radical; a sulphonyl radical; a sulphinyl radical; a phosphonyl radical; a carbamoyl radical; a sulphamoyl radical; a cyano radical; a siloxy radical; an amino radical; an acylamino radical; an acyloxy radical; a carbamoyloxy radical; a sulphonamide radical; an imide radical; a ureido radical; a sulphamoylamino radical; a $(C_1-C_4)$alkoxy-carbonylamino radical; an aryloxycarbonylamino radical; a $(C_1-C_4)$alkoxy-carbonyl radical; an aryloxycarbonyl radical; a carboxyl radical; or a hydroxyl radical;

$R_2$ is a hydrogen atom; a $C_1-C_4$ alkyl radical; a $C_1-C_4$ monohydroxyalkyl radical; a $C_2-C_4$ polyhydroxyalkyl radical; a $C_1-C_4$ aminoalkyl radical; a $(CH_2)_p$—X—$(CH_2)_q$OR' radical in which p and q are identical or different integers ranging from 1 to 3, R' represents a hydrogen atom or a methyl radical, and X denotes an oxygen atom or an NR" group in which R" represents a hydrogen atom or a methyl radical; a $(C_1-C_4)$alkoxy$(C_2-C_4)$alkyl radical; or a di$(C_1-C_4)$alkylamino$(C_1-C_4)$alkyl radical;

$Z_a$, $Z_b$ and $Z_c$ represent, independently of one another, a nitrogen atom or a carbon atom carrying an $R_3$ or $R_4$ radical, where $R_3$ and $R_4$ independently have the same meanings as those indicated above for $R_1$, with the proviso that at least one of the $Z_a$, $Z_b$ and $Z_c$ radicals is other than a carbon atom; $R_3$ and $R_4$ can also together form a substituted or unsubstituted aromatic ring.

2. A composition according to claim 1, wherein said keratinous fibers are human keratinous fibers.

3. A composition according to claim 2, wherein said human keratinous fibers are hair.

4. A composition according to claim 1, wherein, when $R_1$ represents a linear or branched $C_1$–$C_{20}$ alkyl radical substituted by one or two radicals R wherein R is an aryl radical or when $R_1$ is an aryl radical, said aryl radical is phenyl or naphthyl.

5. A composition according to claim 1, wherein $R_1$ represents a 5 or 6 membered heterocycle containing at least one nitrogen, oxygen or sulphur atom and wherein said heterocycle is pyridyl, quinolyl, pyrrolyl, morpholyl, furanyl, tetrahydorfuranyl, pyrazolyl, triazolyl, thiazolyl, oxazolyl, imidazolyl or thiadiazolyl.

6. A composition according to claim 1, wherein $R_1$ is a halogen atom and wherein said halogen is bromine, chlorine, or fluorine.

7. A composition according to claim 1, wherein $R_1$ is a hydrogen atom; a linear or branched $C_1$–$C_4$ alkyl radical; a phenyl ring; a phenyl ring substituted by a halogen atom, a $C_1$–$C_4$ alkyl radical, a $C_1$–$C_4$ alkoxy radical, a nitro radical, an amino radical, a trifluoromethyl radical or by a $C_1$–$C_4$ alkylamino radical; a benzyl radical; a benzyl radical substituted by a halogen atom, a $C_1$–$C_4$ alkyl radical, a $C_1$–$C_4$ alkoxy radical, a nitro radical, an amino radical, a trifluoromethyl radical or by a $C_1$–$C_4$ alkylamino radical; a heterocycle chosen from thiophene, furan or pyridine rings; a trifluoromethyl radical; a $(CH_2)_p$—X—$(CH_2)_q$—OR' radical in which p and q are identical or different integers ranging from 1 to 3, R' represents a hydrogen atom or a methyl radical and X denotes an oxygen atom or an NR" radical in which R" denotes a hydrogen atom or a methyl radical; a $C_1$–$C_4$ hydroxyalkyl radical; a $C_1$–$C_4$ aminoalkyl radical; a $C_1$–$C_4$ alkylamino radical; a di($C_1$–$C_4$)alkylamino radical; an arylamino radical; an alkoxy radical chosen from methoxy, ethoxy and phenoxy; a halogen atom chosen from bromine, chlorine and fluorine; a carboxyl radical; a $C_1$–$C_4$ alkoxycarbonyl radical; a phenyloxycarbonyl radical; a methylthio radical; an ethylthio radical; a phenylthio radical; a methanesulphonyl radical; a cyano radical; an amino radical; or a hydroxyl radical.

8. A composition according to claim 7, wherein $R_1$ is a hydrogen atom; an alkyl radical chosen from methyl, ethyl, isopropyl and tert-butyl radicals; a halogen atom chosen from chlorine and fluorine; a phenyl radical; a toluyl radical; a 4-chlorophenyl radical; a 4-methoxyphenyl radical; a 3-methoxyphenyl radical; a 2-methoxyphenyl radical; a benzyl radical; a heterocycle chosen from pyridyl, furyl and thienyl rings; a trifluoromethyl radical, a hydroxymethyl radical; an aminomethyl radical; a methoxy radical; an ethoxy radical; a methylamino radical; an ethylamino radical; a dimethylamino radical; a carboxyl radical; a methoxycarbonyl radical; an ethoxycarbonyl radical or a cyano radical.

9. A composition according to claim 8, wherein $R_1$ is a hydrogen atom; a chlorine atom; a methyl radical; an ethyl radical; a phenyl radical; a toluyl radical; a 4-chlorophenyl radical; a 4-methoxyphenyl radical; a benzyl radical; a trifluoromethyl radical; a methoxy radical; an ethoxy radical; a carboxyl radical; a methylamino radical; a dimethylamino radical or a cyano radical.

10. A composition according to claim 1, wherein $R_2$ is a hydrogen atom; a methyl radical or a β-hydroxyethyl radical.

11. A composition according to claim 10, wherein $R_2$ is a hydrogen atom.

12. A composition according to claim 1, wherein $R_3$ and $R_4$ are independently a hydrogen atom; a hydroxyl radical; an amino radical; a linear or branched $C_1$–$C_4$ alkyl radical; a trifluoromethyl radical; a phenyl ring; a phenyl ring substituted by one or two radicals R chosen from a halogen atom, a $C_1$–$C_4$ alkyl radical, a $C_1$–$C_4$ alkoxy radical, a hydroxyl radical, a carboxyl radical, a nitro radical, a $C_1$–$C_4$ alkylthio radical, a methylenedioxy radical, an amino radical, a trifluoromethyl radical and a $C_1$–$C_4$ alkylamino radical; a benzyl radical; a benzyl radical substituted by a halogen atom, a methyl or isopropyl radical or a methoxy radical; a $C_1$–$C_4$ monohydroxyalkyl radical; a $C_1$–$C_4$ aminoalkyl radical; a $(C_1$–$C_4)$alkylamino$(C_1$–$C_4)$alkyl radical; an alkoxy radical chosen from methoxy and ethoxy radicals; a phenoxy radical; a methylthio radical; an ethylthio radical; a phenylthio radical; a methanesulphonyl radical; or a substituted or unsubstituted aromatic ring formed jointly by $R_3$ and $R_4$.

13. A composition according to claim 12, wherein $R_3$ and $R_4$ jointly form a substituted or unsubstituted aromatic ring, said ring being a phenyl ring, pyridyl ring or phenyl ring substituted by a sulphonyl radical, a halogen atom, a $C_1$–$C_4$ alkoxy radical, a $C_1$–$C_4$ alkyl radical, a nitro radical, a cyano radical, an amino radical, a $C_1$–$C_4$ alkylamino radical or a trifluoromethyl radical.

14. A composition according to claim 12, wherein $R_3$ and $R_4$ are independently a hydrogen atom; an alkyl radical chosen from methyl, ethyl, isopropyl, n-proply and tert-butyl radicals; a phenyl ring; a toluyl ring; a 2-, 3- or 4-chlorophenyl ring; a 3- or 4-hydroxyphenyl ring; a 3- or 4-aminophenyl ring; a 3- or 4-methoxyphenyl ring; a 4-trifluoromethylphenyl ring; a benzyl ring; a trifluoromethyl radical; a hydroxymethyl radical; a hydroxyethyl radical; a hydroxyisopropyl radical; an aminomethyl or aminoethyl radical; a methoxy or ethoxy radical; a methylthio or ethylthio radical; or a substituted or unsubstituted aromatic ring formed jointly by $R_3$ and $R_4$.

15. A composition according to claim 14, wherein $R_3$ and $R_4$ jointly form a substituted or unsubstituted aromatic ring, said ring being a phenyl, toluyl, sulphonylphenyl or chlorophenyl ring.

16. A composition according to claim 14, wherein $R_3$ and $R_4$ independently are a hydrogen atom; a methyl radical; an ethyl radical; an isopropyl radical; a phenyl ring; a 4-chlorophenyl ring; a 4-methoxyphenyl ring; a 4-aminophenyl ring; a methoxy or ethoxy radical; a methylthio or ethylthio radical; or $R_3$ and $R_4$ jointly form a phenyl ring.

17. A composition according to claim 1, wherein said at least one compound of formula (I) is chosen from:

i) pyrazolo[1,5-b]-1,2,4-triazoles of formula (Ia) and the acid addition salts thereof:

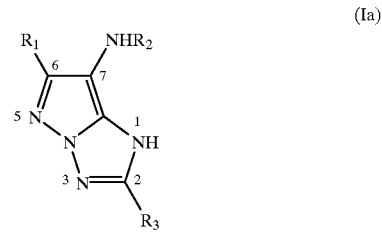

(Ia)

ii) pyrazolo[3,2-c]-1,2,4-triazoles of formula (Ib) and the acid addition salts thereof:

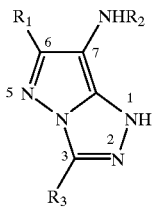

(Ib)

iii) pyrazolotetrazoles of formula (Ic) and the acid addition salts thereof:

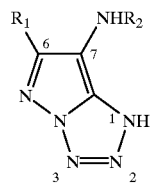

(Ic)

iv) pyrazolo[1,5-a]imidazoles of formula (Id) and the acid addition salts thereof:

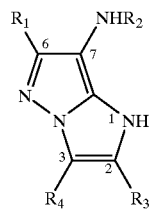

(Id)

v) pyrazolo[5,1-e]pyrazoles of formula (Ie) and the acid addition salts thereof:

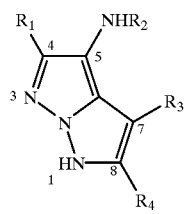

(Ie)

vi) pyrazolo[5,1-e]-1,2,3-triazoles of formula (If) and the acid addition salts thereof:

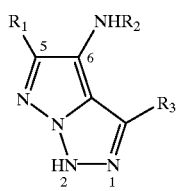

(If)

in which $R_1$, $R_2$, $R_3$ and $R_4$ have the same meanings as those indicated in claim 1.

18. A composition according to claim 17, wherein said pyrazolo[1,5-b]-1,2,4-triazoles of formula (Ia) or said pyrazolo[3,2-c]-1,2,4-triazoles of formula (Ib) are chosen from those compounds in which:
   $R_1$ is a hydrogen atom or a methyl, trifluoromethyl, carboxyl, phenyl, ethoxy, cyano, ethylthio, amino or hydroxyl radical;
   $R_2$ is a hydrogen atom; and
   $R_3$ is a hydrogen atom or a methyl, β-aminoethyl, ethyl, isopropyl, phenyl, β-hydroxyethyl, methylthio or ethoxy radical.

19. A composition according to claim 17, wherein said pyrazolotetrazoles of formula (Ic) are chosen from those compounds in which:
   $R_1$ is a hydrogen atom or a methyl, trifluoromethyl, carboxyl, phenyl, ethoxy or cyano radical; and
   $R_2$ is a hydrogen atom.

20. A composition according to claim 17, wherein said pyrazolo[1,5-a]imidazoles of formula (Id) are chosen from those compounds in which:
   $R_1$ is a hydrogen atom or a methyl, trifluoromethyl, carboxyl, phenyl, ethoxy, cyano, amino, ethylthio or hydroxyl radical;
   $R_2$ is a hydrogen atom; and
   $R_3$ and $R_4$ are respectively a hydrogen atom and a hydrogen atom, a hydrogen atom and a methyl radical, a methyl radical and a hydrogen atom, a hydrogen atom and a phenyl radical, or a hydroxyl radical and a hydrogen atom; or $R_3$ and $R_4$ jointly form a phenyl ring.

21. A composition according to claim 17, wherein said pyrazolo[5,1-e]pyrazoles of formula (Ie) are chosen from those compounds in which:
   $R_1$ is a hydrogen atom or a methyl, trifluoromethyl, carboxyl, phenyl, ethoxy or cyano radical;
   $R_2$ is a hydrogen atom; and
   $R_3$ and $R_4$ respectively are a hydrogen atom and a methyl radical, a methyl radical and a hydrogen atom, a methyl radical and a methyl radical, a hydrogen atom and a phenyl radical, or a hydrogen atom and an amino radical.

22. A composition according to claim 17, wherein said pyrazolo[5,1-e]-1,2,3-triazoles of formula (If) are chosen from those compounds in which:
   $R_1$ is a hydrogen atom or a methyl, trifluoromethyl, carboxyl, phenyl, ethoxy or cyano radical;
   $R_2$ is a hydrogen atom; and
   $R_3$ is a hydrogen atom or a methyl radical.

23. A composition according to claim 1, wherein said at least one compound of formula (I) is chosen from:
   7-amino-2-methylpyrazolo[1,5-b]-1,2,4-triazole;
   7-amino-2-ethylpyrazolo[1,5-b]-1,2,4-triazole;
   7-amino-2-isopropylpyrazolo[1,5-b]-1,2,4-triazole;
   7-amino-2-phenylpyrazolo[1,5-b]-1,2,4-triazole;
   7-amino-2,6-dimethylpyrazolo[1,5-b]-1,2,4-triazole;
   7-amino-6-methyl-2-ethylpyrazolo[1,5-b]-1,2,4-triazole;
   7-amino-6-methyl-2-isopropylpyrazolo[1,5-b]-1,2,4-triazole;
   7-amino-6-methyl-2-phenylpyrazolo[1,5-b]-1,2,4-triazole;
   7-amino-6-carboxy-2-methylpyrazolo[1,5-b]-1,2,4-triazole;
   7-amino-6-carboxy-2-ethylpyrazolo[1,5-b]-1,2,4-triazole;
   7-amino-6-carboxy-2-isopropylpyrazolo[1,5-b]-1,2,4-triazole;
   7-amino-6-carboxy-2-phenylpyrazolo[1,5-b]-1,2,4-triazole;
   7-amino-6-phenyl-2-methylpyrazolo[1,5-b]-1,2,4-triazole;
   7-amino-6-phenyl-2-ethylpyrazolo[1,5-b]-1,2,4-triazole;
   7-amino-6-phenyl-2-isopropylpyrazolo[1,5-b]-1,2,4-triazole;

6,7-diamino-2-methylpyrazolo[1,5-b]-1,2,4-triazole;
6,7-diamino-2-ethylpyrazolo[1,5-b]-1,2,4-triazole;
6,7-diamino-2-isopropylpyrazolo[1,5-b]-1,2,4-triazole;
6,7-diamino-2-phenylpyrazolo[1,5-b]-1,2,4-triazole;
7-amino-6-ethylthio-2-methylpyrazolo[1,5-b]-1,2,4-triazole;
7-amino-6-ethylthio-2-ethylpyrazolo[1,5-b]-1,2,4-triazole;
7-amino-6-ethylthio-2-isopropylpyrazolo[1,5-b]-2,4-triazole;
7-amino-6-ethylthio-2-phenylpyrazolo[1,5-b]-1,2,4-triazole;
7-amino-6-ethoxy-2-methylpyrazolo[1,5-b]-1,2,4-triazole;
7-amino-6-ethoxy-2-ethylpyrazolo[1,5-b]-1,2,4-triazole;
7-amino-6-ethoxy-2-isopropylpyrazolo[1,5-b]-1,2,4-triazole;
7-amino-6-ethoxy-2-phenylpyrazolo[1,5-b]-1,2,4-triazole;
7-amino-6-methyl-2-(2'-aminoethyl)pyrazolo[1,5-b]-1,2,4-triazole;
7-amino-6-carboxy-2-(2'-aminoethyl)pyrazolo[1,5-b]-1,2,4-triazole;
7-amino-6-phenyl-2-(2'-aminoethyl)pyrazolo[1,5-b]-1,2,4-triazole;
7-amino-6-ethylthio-2-(2'-aminoethyl)pyrazolo[1,5-b]-1,2,4-triazole;
7-amino-2-(2'-aminoethyl)pyrazolo[1,5-b]-1,2,4-triazole;
7-amino-2-(2'-hydroxyethyl)pyrazolo[1,5-b]-1,2,4-triazole;
7-amino-6-methyl-2-(2'-hydroxyethyl)pyrazolo[1,5-b]-1,2,4-triazole;
7-amino-6-ethylthio-2-(2'-hydroxyethyl)pyrazolo[1,5-b]-1,2,4-triazole;
7-amino-6-carboxy-2-(2'-hydroxyethyl)pyrazolo[1,5-b]-1,2,4-triazole;
7-amino-6-phenyl-2-(2'-hydroxyethyl)pyrazolo[1,5-b]-1,2,4-triazole;
6,7-diamino-2-(2'-aminoethyl)pyrazolo[1,5-b]-1,2,4-triazole;
6,7-diamino-2-(2'-hydroxyethyl)pyrazolo[1,5-b]-1,2,4-triazole;
7-amino-6-ethoxy-2-(2'-aminoethyl)pyrazolo[1,5-b]-1,2,4-triazole;
7-amino-6-ethoxy-2-(2'-hydroxyethyl)pyrazolo[1,5-b]-1,2,4-triazole;
7-amino-3-methylpyrazolo[3,2-c]-1,2,4-triazole;
7-amino-3-ethylpyrazolo[3,2-c]-1,2,4-triazole;
7-amino-3-isopropylpyrazolo[3,2-c]-1,2,4-triazole;
7-amino-3-phenylpyrazolo[3,2-c]-1,2,4-triazole;
7-amino-3-(2'-aminoethyl)pyrazolo[3,2-c]-1,2,4-triazole;
7-amino-3-(2'-hydroxyethyl)pyrazolo[3,2-c]-1,2,4-triazole;
7-amino-6-methyl-3-ethylpyrazolo[3,2-c]-1,2,4-triazole;
7-amino-3,6-dimethylpyrazolo[3,2-c]-1,2,4-triazole;
7-amino-6-methyl-3-isopropylpyrazolo[3,2-c]-1,2,4-triazole;
7-amino-6-methyl-3-phenylpyrazolo[3,2-c]-1,2,4-triazole;
7-amino-6-methyl-3-(2'-aminoethyl)pyrazolo[3,2-c]-1,2,4-triazole;
7-amino-6-methyl-3-(2'-hydroxyethyl)pyrazolo[3,2-c]-1,2,4-triazole;
7-amino-6-methyl-3-(methylthio)pyrazolo[3,2-c]-1,2,4-triazole;
7-amino-6-phenyl-3-methylpyrazolo[3,2-c]-1,2,4-triazole;
7-amino-6-phenyl-3-ethylpyrazolo[3,2-c]-1,2,4-triazole;
7-amino-6-phenyl-3-isopropylpyrazolo[3,2-c]-1,2,4-triazole;
7-amino-6-phenyl-3-phenylpyrazolo[3,2-c]-1,2,4-triazole;
7-amino-6-phenyl-3-(2'-aminoethyl)pyrazolo[3,2-c]-1,2,4-triazole;
7-amino-6-phenyl-3-(2'-hydroxyethyl)pyrazolo[3,2-c]-1,2,4-triazole;
7-amino-6-phenyl-3-(methylthio)pyrazolo[3,2-c]-1,2,4-triazole;
7-amino-6-ethylthio-3-methylpyrazolo[3,2-c]-1,2,4-triazole;
7-amino-6-ethylthio-3-ethylpyrazolo[3,2-c]-1,2,4-triazole;
7-amino-6-ethylthio-3-isopropylpyrazolo[3,2-c]-1,2,4-triazole;
7-amino-6-ethylthio-3-phenylpyrazolo[3,2-c]-1,2,4-triazole;
7-amino-6-ethylthio-3-(2'-aminoethyl)pyrazolo[3,2-c]-1,2,4-triazole;
7-amino-6-ethylthio-3-(2'-hydroxyethyl)pyrazolo[3,2-c]-1,2,4-triazole;
7-amino-6-trifluoromethyl-3-(methylthio)pyrazolo[3,2-c]-1,2,4-triazole;
7-amino-6-(trifluoromethyl)pyrazolo[3,2-c]-1,2,4-triazole;
7-amino-6-carboxy-3-methylpyrazolo[3,2-c]-1,2,4-triazole;
7-amino-6-carboxy-3-ethylpyrazolo[3,2-c]-1,2,4-triazole;
7-amino-6-carboxy-3-isopropylpyrazolo[3,2-c]-1,2,4-triazole;
7-amino-6-carboxy-3-phenylpyrazolo[3,2-c]-1,2,4-triazole;
7-amino-6-carboxy-3-(2'-aminoethyl)pyrazolo[3,2-c]-1,2,4-triazole;
7-amino-6-carboxy-3-(2'-hydroxyethyl)pyrazolo[3,2-c]-1,2,4-triazole;
6,7-diamino-3-methylpyrazolo[3,2-c]-1,2,4-triazole;
6,7-diamino-3-ethylpyrazolo[3,2-c]-1,2,4-triazole;
6,7-diamino-3-phenylpyrazolo[3,2-c]-1,2,4-triazole;
6,7-diamino-3-isopropylpyrazolo[3,2-c]-1,2,4-triazole;
7-amino-6-ethoxy-3-methylpyrazolo[3,2-c]-1,2,4-triazole;
7-amino-6-ethoxy-3-ethylpyrazolo[3,2-c]-1,2,4-triazole;
7-amino-6-ethoxy-3-isopropylpyrazolo[3,2-c]-1,2,4-triazole;
7-amino-6-ethoxy-3-phenylpyrazolo[3,2-c]-1,2,4-triazole;
7-amino-6-ethoxy-3-(2'-aminoethyl)pyrazolo[3,2-c]-1,2,4-triazole;
7-amino-6-ethoxy-3-(2'-hydroxyethyl)pyrazolo[3,2-c]-1,2,4-triazole;
6,7-diamino-3-(2'-aminoethyl)pyrazolo[3,2-c]-1,2,4-triazole;
6,7-diamino-3-(2'-hydroxyethyl)pyrazolo[3,2-c]-1,2,4-triazole;
7-amino-6-methylpyrazolo[5,1-e]tetrazole;
7-amino-6-phenylpyrazolo[5,1-e]tetrazole;
7-amino-6-carboxypyrazolo[5,1-e]tetrazole;
7-amino-2-methylpyrazolo[1,5-a]imidazole;
7-amino-2-phenylpyrazolo[1,5-a]imidazole;
7-aminopyrazolo[1,5-a]benzimidazole;
7-amino-6-methylpyrazolo[1,5-a]imidazole;
7-amino-2,6-dimethylpyrazolo[1,5-a]imidazole;
7-amino-6-methyl-2-phenylpyrazolo[1,5-a]imidazole;
7-amino-6-methylpyrazolo[1,5-a]benzimidazole;
7-amino-6-phenylpyrazolo[1,5-a]imidazole;
7-amino-6-phenyl-2-methylpyrazolo[1,5-a]imidazole;
7-amino-2,6-diphenylpyrazolo[1,5-a]imidazole;
7-amino-6-phenylpyrazolo[1,5-a]benzimidazole;
7-amino-6-carboxypyrazolo[1,5-a]imidazole;
7-amino-6-carboxy-2-methylpyrazolo[1,5-a]imidazole;
7-amino-6-carboxy-2-phenylpyrazolo[1,5-a]imidazole;
7-amino-6-carboxypyrazolo[1,5-a]benzimidazole;
7-amino-6-ethoxypyrazolo[1,5-a]imidazole;
7-amino-6-ethoxy-2-methylpyrazolo[1,5-a]imidazole;
7-amino-6-ethoxy-2-phenylpyrazolo[1,5-a]imidazole;
7-amino-6-ethoxypyrazolo[1,5-a]benzimidazole;
7-amino-6-(trifluoromethyl)pyrazolo[1,5-a]benzimidazole;
7-amino-6-aminopyrazolo[1,5-a]imidazole;
7-amino-6-amino-2-methylpyrazolo[1,5-a]imidazole;

7-amino-6-amino-2-phenylpyrazolo[1,5-a]imidazole;
7-amino-6-aminopyrazolo[1,5-a]benzimidazole;
7-amino-6-(ethylthio)pyrazolo[1,5-a]imidazole;
7-amino-6-ethylthio-2-methylpyrazolo[1,5-a]imidazole;
7-amino-6-ethylthio-2-phenylpyrazolo[1,5-a]imidazole;
7-amino-6-methyl-2-hydroxypyrazolo[1,5-a]imidazole;
7-amino-6-phenyl-2-hydroxypyrazolo[1,5-a]imidazole;
7-amino-6-ethoxy-2-hydroxypyrazolo[1,5-a]imidazole;
7-amino-6-ethylthio-2-hydroxypyrazolo[1,5-a]imidazole;
6,7-diamino-2-hydroxypyrazolo[1,5-a]imidazole;
5,8-diamino-4-methylpyrazolo[5,1-e]pyrazole;
5,7,8-triamino-4-methylpyrazolo[5,1-e]pyrazole;
6-amino-5-methylpyrazolo[5,1-e]-1,2,3-triazole;
6-amino-5-phenylpyrazolo[5,1-e]-1,2,3-triazole;
and the acid addition salts thereof.

24. A composition according to claim 17, wherein said pyrazolo[1,5-b]-1,2,4-triazoles of formula (Ia) are chosen from:
7-amino-2-methylpyrazolo[1,5-b]-1,2,4-triazole;
7-amino-2-ethylpyrazolo[1,5-b]-1,2,4-triazole;
7-amino-2-isopropylpyrazolo[1,5-b]-1,2,4-triazole;
7-amino-2-phenylpyrazolo[1,5-b]-1,2,4-triazole;
7-amino-2,6-dimethylpyrazolo[1,5-b]-1,2,4-triazole;
7-amino-6-methyl-2-ethylpyrazolo[1,5-b]-1,2,4-triazole;
7-amino-6-methyl-2-isopropylpyrazolo[1,5-b]-1,2,4-triazole;
7-amino-6-methyl-2-phenylpyrazolo[1,5-b]-1,2,4-triazole;
7-amino-6-carboxy-2-methylpyrazolo[1,5-b]-1,2,4-triazole;
7-amino-6-carboxy-2-ethylpyrazolo[1,5-b]-1,2,4-triazole;
7-amino-6-carboxy-2-isopropylpyrazolo[1,5-b]-1,2,4-triazole;
7-amino-6-carboxy-2-phenylpyrazolo[1,5-b]-1,2,4-triazole;
7-amino-6-phenyl-2-methylpyrazolo[1,5-b]-1,2,4-triazole;
7-amino-6-phenyl-2-ethylpyrazolo[1,5-b]-1,2,4-triazole;
7-amino-6-phenyl-2-isopropylpyrazolo[1,5-b]-1,2,4-triazole;
6,7-diamino-2-methylpyrazolo[1,5-b]-1,2,4-triazole;
6,7-diamino-2-ethylpyrazolo[1,5-b]-1,2,4-triazole;
6,7-diamino-2-isopropylpyrazolo[1,5-b]-1,2,4-triazole;
6,7-diamino-2-phenylpyrazolo[1,5-b]-1,2,4-triazole;
7-amino-6-ethylthio-2-methylpyrazolo[1,5-b]-1,2,4-triazole;
7-amino-6-ethylthio-2-ethylpyrazolo[1,5-b]-1,2,4-triazole;
7-amino-6-ethylthio-2-isopropylpyrazolo[1,5-b]-1,2,4-triazole;
7-amino-6-ethylthio-2-phenylpyrazolo[1,5-b]-1,2,4-triazole;
7-amino-6-ethoxy-2-methylpyrazolo[1,5-b]-1,2,4-triazole;
7-amino-6-ethoxy-2-ethylpyrazolo[1,5-b]-1,2,4-triazole;
7-amino-6-ethoxy-2-isopropylpyrazolo[1,5-b]-1,2,4-triazole;
7-amino-6-ethoxy-2-phenylpyrazolo[1,5-b]-1,2,4-triazole;
7-amino-6-methyl-2-(2'-aminoethyl)pyrazolo[1,5-b]-1,2,4-triazole;
7-amino-6-carboxy-2-(2'-aminoethyl)pyrazolo[1,5-b]-1,2,4-triazole;
7-amino-6-phenyl-2-(2'-aminoethyl)pyrazolo[1,5-b]-1,2,4-triazole;
7-amino-6-ethylthio-2-(2'-aminoethyl)pyrazolo[1,5-b]-1,2,4-triazole;
7-amino-2-(2'-aminoethyl)pyrazolo[1,5-b]-1,2,4-triazole;
7-amino-2-(2'-hydroxyethyl)pyrazolo[1,5-b]-1,2,4-triazole;
7-amino-6-methyl-2-(2'-hydroxyethyl)pyrazolo[1,5-b]-1,2,4-triazole;
7-amino-6-ethylthio-2-(2'-hydroxyethyl)pyrazolo[1,5-b]-1,2,4-triazole;
7-amino-6-carboxy-2-(2'-hydroxyethyl)pyrazolo[1,5-b]-1,2,4-triazole;
7-amino-6-phenyl-2-(2'-hydroxyethyl)pyrazolo[1,5-b]-1,2,4-triazole;
6,7-diamino-2-(2'-aminoethyl)pyrazolo[1,5-b]-1,2,4-triazole;
6,7-diamino-2-(2'-hydroxyethyl)pyrazolo[1,5-b]-1,2,4-triazole;
7-amino-6-ethoxy-2-(2'-aminoethyl)pyrazolo[1,5-b]-1,2,4-triazole;
7-amino-6-ethoxy-2-(2'-hydroxyethyl)pyrazolo[1,5-b]-1,2,4-triazole;
and the acid addition salts thereof.

25. A composition according to claim 17, wherein said pyrazolo[3,2-c]-1,2,4-triazoles of formula (Ib) are chosen from:
7-amino-3-methylpyrazolo[3,2-c]-1,2,4-triazole;
7-amino-3-ethylpyrazolo[3,2-c-]1,2,4-triazole;
7-amino-3-isopropylpyrazolo[3,2-c]-1,2,4-triazole;
7-amino-3-phenylpyrazolo[3,2-c]-1,2,4-triazole;
7-amino-3-(2'-aminoethyl)pyrazolo[3,2-c]-1,2,4-triazole;
7-amino-3-(2'-hydroxyethyl)pyrazolo[3,2-c]-1,2,4-triazole;
7-amino-6-methyl-3-ethylpyrazolo[3,2-c]-1,2,4-triazole;
7-amino-3,6-dimethylpyrazolo[3,2-c]-1,2,4-triazole;
7-amino-6-methyl-3-isopropylpyrazolo[3,2-c]-1,2,4-triazole;
7-amino-6-methyl-3-phenylpyrazolo[3,2-c]-1,2,4-triazole;
7-amino-6-methyl-3-(2'-aminoethyl)pyrazolo[3,2-c]-1,2,4-triazole;
7-amino-6-methyl-3-(2'-hydroxyethyl)pyrazolo[3,2-c]-1,2,4-triazole;
7-amino-6-methyl-3-(methylthio)pyrazolo[3,2-c]-1,2,4-triazole;
7-amino-6-phenyl-3-methylpyrazolo[3,2-c]-1,2,4-triazole;
7-amino-6-phenyl-3-ethylpyrazolo[3,2-c]-1,2,4-triazole;
7-amino-6-phenyl-3-isopropylpyrazolo[3,2-c]-1,2,4-triazole;
7-amino-6-phenyl-3-phenylpyrazolo[3,2-c]-1,2,4-triazole;
7-amino-6-phenyl-3-(2'-aminoethyl)pyrazolo[3,2-c]-1,2,4-triazole;
7-amino-6-phenyl-3-(2'-phydroxyethy)pyrazolo[3,2-c]-1,2,4-triazole;
7-amino-6-phenyl-3-(methylthio)pyrazolo[3,2-c]-1,2,4-triazole;
7-amino-6-ethylthio-3-methylpyrazolo[3,2-c]-1,2,4-triazole;
7-amino-6-ethylthio-3-ethylpyrazolo[3,2-c]-1,2,4-triazole;
7-amino-6-ethylthio-3-isopropylpyrazolo[3,2-c]-1,2,4-triazole;
7-amino-6-ethylthio-3-phenylpyrazolo[3,2-c]-1,2,4-triazole;
7-amino-6-ethylthio-3-(2'-aminoethyl)pyrazolo[3,2-c]-1,2,4-triazole;
7-amino-6-ethylthio-3-(2'-hydroxyethyl)pyrazolo[3,2-c]-1,2,4-triazole;
7-amino-6-trifluoromethyl-3-(methylthio)pyrazolo[3,2-c]-1,2,4-triazole;
7-amino-6-(trifluoromethyl)pyrazolo[3,2-c]-1,2,4-triazole;
7-amino-6-carboxy-3-methylpyrazolo[3,2-c]-1,2,4-triazole;
7-amino-6-carboxy-3-ethylpyrazolo[3,2-c]-1,2,4-triazole;
7-amino-6-carboxy-3-isopropylpyrazolo[3,2-c]-1,2,4-triazole;
7-amino-6-carboxy-3-phenylpyrazolo[3,2-c]-1,2,4-triazole;
7-amino-6-carboxy-3-(2'-aminoethyl)pyrazolo[3,2-c]-1,2,4-triazole;
7-amino-6-carboxy-3-(2'-hydroxyethyl)pyrazolo[3,2-c]-1,2,4-triazole;
6,7-diamino-3-methylpyrazolo[3,2-c]-1,2,4-triazole;
6,7-diamino-3-ethylpyrazolo[3,2-c]-1,2,4-triazole;

6,7-diamino-3-phenylpyrazolo[3,2-c]-1,2,4-triazole;
6,7-diamino-3-isopropylpyrazolo[3,2-c]-1,2,4-triazole;
7-amino-6-ethoxy-3-methylpyrazolo[3,2-c]-1,2,4-triazole;
7-amino-6-ethoxy-3-ethylpyrazolo[3,2-c]-1,2,4-triazole;
7-amino-6-ethoxy-3-isopropylpyrazolo[3,2-c]-1,2,4-triazole;
7-amino-6-ethoxy-3-phenylpyrazolo[3,2-c]-1,2,4-triazole;
7-amino-6-ethoxy-3-(2'-aminoethyl)pyrazolo[3,2-c]-1,2,4-triazole;
7-amino-6-ethoxy-3-(2'-hydroxyethyl)pyrazolo[3,2-c]-1,2,4-triazole;
6,7-diamino-3-(2'-aminoethyl)pyrazolo[3,2-c]-1,2,4-triazole;
6,7-diamino-3-(2'-hydroxyethyl)pyrazolo[3,2-c]-1,2,4-triazole;
and the acid addition salts thereof.

26. A composition according to claim 17, wherein said pyrazolotetrazoles of formula (Ic) are chosen from:
7-amino-6-methylpyrazolo[5,1-e]tetrazole;
7-amino-6-phenylpyrazolo[5,1-e]tetrazole;
7-amino-6-carboxypyrazolo[5,1-e]tetrazole;
and the acid addition salts thereof.

27. A composition according to claim 17, wherein said pyrazolo[1,5-a]imidazoles of formula (Id) are chosen from:
7-amino-2-methylpyrazolo[1,5-a]imidazole;
7-amino-2-phenylpyrazolo[1,5-a]imidazole;
7-aminopyrazolo[1,5-a]benzimidazole;
7-amino-6-methylpyrazolo[1,5-a]imidazole;
7-amino-2,6-dimethylpyrazolo[1,5-a]imidazole;
7-amino-6-methyl-2-phenylpyrazolo[1,5-a]imidazole;
7-amino-6-methylpyrazolo[1,5-a]benzimidazole;
7-amino-6-phenylpyrazolo[1,5-a]imidazole;
7-amino-6-phenyl-2-methylpyrazolo[1,5-a]imidazole;
7-amino-2,6-diphenylpyrazolo[1,5-a]imidazole;
7-amino-6-phenylpyrazolo[1,5-a]benzimidazole;
7-amino-6-carboxypyrazolo[1,5-a]imidazole;
7-amino-6-carboxy-2-methylpyrazolo[1,5-a]imidazole;
7-amino-6-carboxy-2-phenylpyrazolo[1,5-a]imidazole;
7-amino-6-carboxypyrazolo[1,5-a]benzimidazole;
7-amino-6-ethoxypyrazolo[1,5-a]imidazole;
7-amino-6-ethoxy-2-methylpyrazolo[1,5-a]imidazole;
7-amino-6-ethoxy-2-phenylpyrazolo[1,5-a]imidazole;
7-amino-6-ethoxypyrazolo[1,5-a]benzimidazole;
7-amino-6-(trifluoromethyl)pyrazolo[1,5-a]benzimidazole;
7-amino-6-aminopyrazolo[1,5-a]imidazole;
7-amino-6-amino-2-methylpyrazolo[1,5-a]imidazole;
7-amino-6-amino-2-phenylpyrazolo[1,5-a]imidazole;
7-amino-6-aminopyrazolo[1,5-a]benzimidazole;
7-amino-6-(ethylthio)pyrazolo[1,5-a]imidazole;
7-amino-6-ethylthio-2-methylpyrazolo[1,5-a]imidazole;
7-amino-6-ethylthio-2-phenylpyrazolo[1,5-a]imidazole;
7-amino-6-methyl-2-hydroxypyrazolo[1,5-a]imidazole;
7-amino-6-phenyl-2-hydroxypyrazolo[1,5-a]imidazole;
7-amino-6-ethoxy-2-hydroxypyrazolo[1,5-a]imidazole;
7-amino-6-ethylthio-2-hydroxypyrazolo[1,5-a]imidazole;
6,7-diamino-2-hydroxypyrazolo[1,5-a]imidazole;
and the acid addition salts thereof.

28. A composition according to claim 17, wherein said pyrazolo[5,1-e]pyrazoles of formula (Ie) are chosen from:
5,8-diamino-4-methylpyrazolo[5,1-e]pyrazole;
5,7,8-triamino-4-methylpyrazolo[5,1-e]pyrazole;
and the acid addition salts thereof.

29. A composition according to claim 17, wherein said pyrazolo[5,1-e]-1,2,3-triazoles of formula (If) are chosen from:
6-amino-5-methylpyrazolo[5,1-e]-1,2,3-triazole;
6-amino-5-phenylpyrazolo[5,1-e]-1,2,3-triazole;
and the acid addition salts thereof.

30. A composition according to claim 1, wherein said at least one compound of formula (I) is present in an amount ranging from 0.0005 to 12% by weight relative to the total weight of said composition.

31. A composition according to claim 30, wherein said at least one compound of formula (I) is present in an amount ranging from 0.005 to 6% by weight relative to the total weight of said composition.

32. A composition according to claim 1, wherein said medium suitable for dyeing comprises water, a water/alcohol mixture or a mixture of water and of at least one organic solvent.

33. A composition according to claim 32, wherein said at least one organic solvent is a $C_1$–$C_4$ lower alkanol, a glycerol, a glycol, a glycol ether, an aromatic alcohol, or a mixture thereof.

34. A composition according to claim 32, wherein said at least one organic solvent represents from 1 to 40% by weight relative to the total weight of said composition.

35. A composition according to claim 1, wherein said composition has a pH ranging from 3 to 12.

36. A composition according to claim 35, wherein said composition has a pH ranging from 5 to 11.

37. A composition according to claim 1, wherein said composition further contains at least one coupler.

38. A composition according to claim 37, wherein said at least one coupler is chosen from an aromatic diamine, a meta-aminophenol, a meta-diphenol and a heterocyclic coupler.

39. A composition according to claim 37, wherein said at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethyl)amino-1-methoxybenzene, 1,3-diaminobenzene, 1,3-bis(2,4-diaminophenoxy)-propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, and the acid addition salts thereof.

40. A composition according to claim 37, wherein said at least one coupler is present in an amount ranging from 0.0001 to 10% by weight relative to the total weight of said composition.

41. A composition according to claim 40, wherein said at least one coupler is present in an amount ranging from 0.005 to 5% by weight relative to the total weight of said composition.

42. A composition according to claim 1, wherein said composition further comprises at least one additional oxidation base.

43. A composition according to claim 42, wherein said at least one additional oxidation base is chosen from a para-phenylenediamine, a bisphenylalkylenediamine, a para-aminophenol, an ortho-aminophenol and a heterocyclic base other than said pyrazoloazole compounds of formula (I).

44. A composition according to claim 42, wherein said at least one additional oxidation base is present in an amount ranging from 0.0005 to 12% by weight relative to the total weight of said composition.

45. A composition according to claim 1, wherein said at least one acid addition salt is a hydrochloride, a hydrobromide, a sulphate, a citrate, a succinate, a tartrate, a tosylate, a benzenesulphonate, a lactate or an acetate.

46. A composition according to claim 1, wherein said composition additionally contains at least one direct dye.

47. A method for dyeing keratinous fibers comprising contacting said fibers with at least one oxidation dye composition according to claim 1, in the presence of air or an oxidizing agent, for a time sufficient to achieve color development.

48. The method according to claim 47, wherein said keratinous fibers are human keratinous fibers.

49. The method according to claim 48, wherein said human keratinous fibers are hair.

50. A method according to claim 47, wherein said color development is achieved without an oxidizing agent, but with contact only with atmospheric oxygen.

51. The method according to claim 47, wherein said dye composition is mixed at the time of use with an oxidizing composition comprising, in a medium suitable for dyeing, at least one oxidizing agent present in an amount sufficient for color development.

52. The method according to claim 47, wherein said dye composition additionally contains at least one oxidation catalyst.

53. The method according to claim 52, wherein said at least one oxidation catalyst is a metal salt.

54. The method according to claim 53, wherein said metal salt is manganese, cobalt, copper, iron, silver or zinc.

55. The method according to claim 53, wherein said metal salt is manganese diacetate tetrahydrate, manganese dichloride, manganese triacetate or a hydrate thereof, manganese trichloride, zinc dichloride, zinc diacetate dihydrate, zinc carbonate, zinc dinitrate, zinc sulphate, iron dichloride, iron sulphate, iron diacetate, cobalt diacetate tetrahydrate, cobalt carbonate, cobalt dichloride, cobalt sulphate heptahydrate, cupric chloride or ammoniacal silver nitrate.

56. The method according to claim 53, wherein said metal salt is present in an amount ranging from 0.001 to 4% by weight relative to the total weight of said dye composition.

57. The method according to claim 56, wherein said metal salt is present in an amount ranging from 0.005 to 2% by weight relative to the total weight of said dye composition.

58. The method according to claim 51, wherein said at least one oxidizing agent is hydrogen peroxide, urea hydrogen peroxide, an alkali metal bromate, a persalt, or an enzyme.

59. The method according to claim 58, wherein said persalt is a perborate or a persulphate.

60. The method according to claim 58, wherein said enzyme is a peroxidase or an oxidoreductase with 2 unpaired electrons.

61. The method according to claim 47, wherein said color is developed at acidic, neutral, or alkaline pH with an oxidizing agent which is added to said oxidation dyeing composition at the time of application or which is present in an oxidizing composition that is applied:

(i) separately from the dye composition at the same time that said dye composition is applied to said fibers, or (ii) sequentially with the dye composition.

62. The method according to claim 47, wherein said time ranges from 3 to 50 minutes.

63. The method according to claim 62, wherein said time ranges from 5 to 30 minutes.

64. The method according to claim 51, wherein said oxidizing composition has a pH ranging from 3 to 12.

65. The method according to claim 64, wherein said oxidizing composition has a pH ranging from 5 to 11.

66. The composition according to claim 1, said composition being in the form of a liquid, a cream, a gel or any other form suitable for dyeing keratinous fibers.

67. A multi-compartment dyeing device or kit for dyeing keratin fibers, comprising at least two compartments, a first compartment of which contains a dyeing composition according to claim 1 and a second compartment of which contains an oxidizing composition.

* * * * *

UNITED STATES PATENT AND TRADEMARK OFFICE
CERTIFICATE OF CORRECTION

PATENT NO. : 6,379,397 B2
DATED : April 30, 2002
INVENTOR(S) : Vidal et al.

It is certified that error appears in the above-identified patent and that said Letters Patent is hereby corrected as shown below:

Column 28,
Line 36, please change "ring:a" to read -- ring; a --.

Column 29,
Ine 14, please change "tetrahydorfuranyl" to read -- tetrahydrofuranyl --.

Column 30,
Line 30, please change "n-proply" to read -- n-propyl --.

Column 33,
Line 8, please change "[1,5-b]-" to read -- [1,5-b]-1, --.

Column 36,
Line 16, after "[3,2-c]" please insert a hyphen.
Line 39, please change "phydroxyethy" to read -- hydroxyethyl --.

Signed and Sealed this

Third Day of September, 2002

Attest:

*Attesting Officer*

JAMES E. ROGAN
*Director of the United States Patent and Trademark Office*